(12) United States Patent
Philips et al.

(10) Patent No.: US 12,716,904 B2
(45) Date of Patent: Aug. 25, 2026

(54) COMPOSITIONS AND METHODS FOR THE DETECTION OF TUBERCULOSIS

(71) Applicant: Washington University, St. Louis, MO (US)

(72) Inventors: Jennifer Philips, St. Louis, MO (US); Pallavi Chandra, St. Louis, MO (US); Heloise Coullon, St. Louis, MO (US)

(73) Assignee: Washington University, St. Louis, MO (US)

( * ) Notice: Subject to any disclaimer, the term of this patent is extended or adjusted under 35 U.S.C. 154(b) by 476 days.

(21) Appl. No.: 18/278,740

(22) PCT Filed: Feb. 24, 2022

(86) PCT No.: PCT/US2022/017675
§ 371 (c)(1),
(2) Date: Aug. 24, 2023

(87) PCT Pub. No.: WO2022/182854
PCT Pub. Date: Sep. 1, 2022

(65) Prior Publication Data

US 2024/0142475 A1 May 2, 2024

Related U.S. Application Data

(60) Provisional application No. 63/153,015, filed on Feb. 24, 2021.

(51) Int. Cl.
*G01N 33/92* (2006.01)

(52) U.S. Cl.
CPC ......... *G01N 33/92* (2013.01); *G01N 2405/02* (2013.01); *G01N 2800/52* (2013.01)

(58) Field of Classification Search
None
See application file for complete search history.

(56) References Cited

U.S. PATENT DOCUMENTS

2009/0111125 A1* 4/2009 Verschoor .......... G01N 33/5695 436/501
2012/0064624 A1* 3/2012 Lu .......................... A61P 31/06 435/375
2016/0145696 A1 5/2016 Brandon et al.
(Continued)

FOREIGN PATENT DOCUMENTS

WO 2019236768 A1 12/2019

OTHER PUBLICATIONS

Chandra P., et al., "Macrophage Global Metabolomics Identifies Cholestenone as Host/Pathogen Cometabolite Present in Human Mycobacterium Tuberculosis Infection," The Journal of Clinical Investigation, Feb. 1, 2022, vol. 132, No. 3, pp. 1-15.
(Continued)

*Primary Examiner* — Jennifer Wecker
*Assistant Examiner* — Tracy Ching-Tian Colena
(74) *Attorney, Agent, or Firm* — Polsinelli PC

(57) ABSTRACT

Methods for diagnosis of bacterial infections (e.g., tuberculosis) are disclosed. In particular, the disclosure relates to the use of a panel of biomarkers for aiding diagnosis, prognosis, and treatment of bacterial infections such as tuberculosis. The identified biomarkers can be used to detect active infection as well as bacterial burden, and for monitoring responses to treatment.

20 Claims, 19 Drawing Sheets

Global Metabolomic Profiling
4 h
3 h
24h

(56) References Cited

U.S. PATENT DOCUMENTS

| | | | |
|---|---|---|---|
| 2018/0291452 | A1 | 10/2018 | Khatri et al. |
| 2019/0391146 | A1 | 12/2019 | Sampson et al. |

OTHER PUBLICATIONS

Driscoll M.D., et al., "Structural and Biochemical Characterization of *Mycobacterium tuberculosis* CYP142: Evidence for Multiple Cholesterol 27-Hydroxylase Activities in a Human Pathogen," The Journal of Biological Chemistry, Dec. 3, 2010, vol. 285, No. 49, pp. 38270-38282.

International Search Report and Written Opinion for Application No. PCT/US2022/017675, mailed on Jun. 29, 2022, 18 pages.

* cited by examiner

COMPOSITIONS AND METHODS FOR THE DETECTION OF TUBERCULOSIS

CROSS REFERENCE TO RELATED APPLICATIONS

This application claims the priority of U.S. Provisional application No. 63/153,015, filed Feb. 24, 2021, the disclosure each of which is hereby incorporated by reference in its entirety.

GOVERNMENTAL RIGHTS

This invention was made with government support under AI128427 and AI160386 awarded by the National Institutes of Health. The government has certain rights in the invention.

FIELD OF THE TECHNOLOGY

The present disclosure pertains generally to methods for detection of infectious bacteria expressing the enzyme 3β-hydroxysteroid dehydrogenase (e.g., *Mycobacterium tuberculosis, Mycobacterium leprae, Nocardia, Rhodococcus*). In particular, the disclosure relates to biomarkers that can be used to inform diagnosis of infection, select subjects for further diagnostic testing, and guide treatment decisions.

BACKGROUND

Tuberculosis (TB) is a worldwide public health issue, with 9 million new infections and 1.5 million deaths in 2013 (Global Tuberculosis Programme, World Health Organization. Global tuberculosis report. Geneva, Switzerland: World Health Organization; 2012: volumes). Despite advances in diagnosis and treatment, there is still a large burden of disease. TB is difficult to accurately diagnose; traditional methods such as tuberculin skin testing and interferon gamma release assays (IGRAs) are unable to distinguish between latent TB and active TB and have lower sensitivity in HIV-positive patients. Although the Xpert MTB/RIF assay has significantly improved diagnostic power, it suffers from reduced accuracy in HIV-positive patients and is not useful for monitoring treatment response (Steingart et al. (2014) Cochrane Database Syst. Rev. 1:CD009593; Friedrich et al. (2013) Lancet Respir. Med 1:462-470).

Several studies have investigated the host response to tuberculosis infection using microarray-based whole genome expression profiles in peripheral blood. However, the results from these studies have not translated into clinical practice so far, due largely to poor generalizability. For instance, different gene signatures, with minimal overlap, have been proposed for distinguishing active TB from other diseases or latent TB and in children and adults (Anderson et al. (2014) N. Engl. J. Med. 370:1712-1723; Kaforou et al. (2014) J. Infect 69 Suppl. 1:S28-31).

The treatment of TB is often challenging and requires multiple antibiotics for at least 4-6 months, and relapse occurs in 3-5% of patients. Long antibiotic courses unnecessarily expose some patients to side effects, while for others, stopping therapy prematurely leads to relapse. As such, there is a large need for new therapies; rapid, sensitive, and affordable diagnostics; and biomarkers to guide clinical decision making.

Accordingly, there remains a need in the art for improved methods to detect infection and monitor response to treatment.

SUMMARY

In an aspect, the present disclosure encompasses a method for diagnosing tuberculosis, a non-tuberculous mycobacteria, a *Rhodococcus* infection or a *Nocardia* infection in a subject. In some embodiments, the method generally includes a) obtaining a biological sample from the subject; b) measuring levels of one or more of cholesterol, an oxidated cholesterol derivative, an oxysterol, a 3β-hyrdoxycholestenoic acid, 3-oxocholestenoic acid, and a 3-oxo-oxysterol, in the biological sample; and c) diagnosing the subject with tuberculosis by analyzing the levels of expression of one or more of cholesterol, an oxidated cholesterol derivative, an oxysterol, and 3-oxo-oxysterol in conjunction with respective reference values from a healthy control, wherein increased levels of the oxidated cholesterol derivative, 3-oxocholestenoic acid, and/or 3-oxo-oxysterol compared to the reference value indicate that the subject has tuberculosis.

In some embodiments, the biological sample is selected from plasma and/or sputum. In some embodiments, when the level of cholesterol decreases relative to a healthy control indicates the subject has tuberculosis. In some embodiments, the oxidated cholesterol derivative is cholestenone, and the methods include determining the ratio value of cholestenone to cholesterol. In some embodiments, an increase in the cholestenone to cholesterol ratio indicates the subject has tuberculosis. In one embodiments, the level of cholestenone is determined from a sputum sample obtained from the subject and the level of cholesterol is determined from a plasma sample obtained from the subject. In another embodiment, the level of cholestenone and the level of cholesterol are determined from a plasma sample obtained from the subject.

In some embodiments, the oxysterol is one or more of 25-hydroxycholesterol, 7α25-hydroxycholesterol, 7α-hydroxycholesterol, 7α27-hydroxycholesterol, and 27-hydroxycholesterol. In some embodiments, the 3-oxo-oxysterol is one or more of 25-hydroxycholestenone, 7α25-hydroxycholestenone, 7α-hydroxycholestenone, 7α27-hydroxycholestenone, and 27-hydroxycholestenone. In some embodiments, the methods include determining the ratio value of 3-oxocholestenoic acid to 3β-hyroxycholestenoic acid, where an increase in the 3-oxocholestenoic acid to 3β-hyroxycholestenoic acid ratio value indicates the subject has tuberculosis.

In some embodiments, the methods include determining the ratio value of 3-oxo-oxysterol to 3β-hyroxy-oxysterol. In one embodiment, the ratio value of 3-oxo-oxysterol to 3β-hyroxy-oxysterol is the ratio value of one or more of 25-hydroxycholestenone to 25-hydroxycholesterol ratio, 7α25-hydroxycholestenone to α25-hydroxycholesterol ratio, 7α-hydroxycholestenone to 7α-hydroxycholesterol ratio, 7α27-hydroxycholestenone to 7α27-hydroxycholesterol ratio, and 27-hydroxycholestenone to 27-hydroxycholesterol ratio. In some embodiments, an increase in the ratio value of 3-oxo-oxysterol to 3β-hyroxy-oxysterol indicates the subject has tuberculosis.

In each of the above embodiments, the levels of one or more of cholesterol, an oxidated cholesterol derivative, an oxysterol, a 3β-hyrdoxycholestenoic acid, 3-oxocholestenoic acid, and a 3-oxo-oxysterol can be determined using liquid chromatography-high resolution mass spectrometry.

In some embodiments, the subject is at risk of developing tuberculosis, a subject with signs and/or symptoms of tuberculosis, or a subject diagnosed with tuberculosis.

In some embodiments, the method further comprises detecting the levels of one or more of itaconate, methylsuccinate, methylcitrate, 2-aminoadipate, and propionylcarnitine.

In another aspect, the present disclosure provides a method for treating a subject with tuberculosis or a non-tuberculous mycobacteria infection, *Rhodococcus* infection or *Nocardia* infection, the method generally includes a) obtaining a biological sample from the subject; b) measuring levels of one or more of cholesterol, an oxidated cholesterol derivative, an oxysterol, a 3β-hyrdoxycholestenoic acid, 3-oxocholestenoic acid, and a 3-oxo-oxysterol, in the biological sample: c) diagnosing the patient with tuberculosis by analyzing the levels of expression of one or more of cholesterol, an oxidated cholesterol derivative, an oxysterol, and 3-oxo-oxysterol in conjunction with respective reference values from a healthy control, wherein increased levels of the oxidated cholesterol derivative 3-oxocholestenoic acid, and/or 3-oxo-oxysterol compared to the reference value indicate that the subject has tuberculosis; and d) administering a treatment to the subject diagnosed according to step c).

In some embodiments, the biological sample is selected from plasma and/or sputum. In some embodiments, when the level of cholesterol decreases relative to a healthy control indicates the subject has an infection. In some embodiments, the oxidated cholesterol derivative is cholestenone. In some embodiments, the method includes determining the ratio value of cholestenone to cholesterol where an increase in the cholestenone to cholesterol ratio indicates the subject has an infection. In one embodiment, the level of cholestenone is determined from a sputum sample obtained from the subject and the level of cholesterol is determined from a plasma sample obtained from the subject. In another embodiment, the level of cholestenone and the level of cholesterol is determined from a plasma sample obtained from the subject.

In some embodiments, the oxysterol is one or more of 25-hydroxycholesterol, 7α25-hydroxycholesterol, 7α-hydroxycholesterol, 7α27-hydroxycholesterol, and 27-hydroxycholesterol. In some embodiments, the 3-oxo-oxysterol is one or more of 25-hydroxycholestenone, 7α25-hydroxycholestenone, 7α-hydroxycholestenone, 7α27-hydroxycholestenone, and 27-hydroxycholestenone. In some embodiments, the methods include determining the ratio value of 3-oxocholestenoic acid to 3β-hyroxycholestenoic acid where an increase in the 3-oxocholestenoic acid to 3β-hyroxycholestenoic acid ratio value indicates the subject has an infection.

In some embodiments, the methods include determining the ratio value of 3-oxo-oxysterol to 3β-hyroxy-oxysterol where the ratio value of 3-oxo-oxysterol to 3β-hyroxy-oxysterol is the ratio value of one or more of 25-hydroxycholestenone to 25-hydroxycholesterol ratio, 7α25-hydroxycholestenone to α25-hydroxycholesterol ratio, 7α-hydroxycholestenone to 7α-hydroxycholesterol ratio, 7α27-hydroxycholestenone to 7α27-hydroxycholesterol ratio, and 27-hydroxycholestenone to 27-hydroxycholesterol ratio. In some embodiments, an increase in the ratio value of 3-oxo-oxysterol to 3β1-hyroxy-oxysterol indicates the subject has an infection.

In each of the above embodiments, the levels of one or more of cholesterol, an oxidated cholesterol derivative, an oxysterol, a 3β-hyrdoxycholestenoic acid, 3-oxocholestenoic acid, and a 3-oxo-oxysterol can be determined using liquid chromatography-high resolution mass spectrometry.

In some embodiments, subject is at risk of developing an infection, a subject with signs and/or symptoms of an infection, or a subject diagnosed with an infection.

In some embodiments, the method further comprises detecting the levels of one or more of itaconate, methylsuccinate, methylcitrate, 2-aminoadipate, and propionylcarnitine.

In some embodiments, the methods include administering an effective amount of at least one antibiotic is selected from the group consisting of rifampicin, isoniazid, pyrazinamide, and ethambutol when the subject is diagnosed with tuberculosis. In some embodiments the methods include administering an effective amount of a corticosteroid if the patient is diagnosed with tuberculosis.

In yet another aspect, the present disclosure provides a method of measuring a treatment response in a subject having or at risk of having tuberculosis or a non-tuberculous mycobacteria infection, *Rhodococcus* infection or *Nocardia* infection, the method generally includes a) quantifying, in a first biological sample obtained from the subject, levels of one or more of cholesterol, an oxidated cholesterol derivative, an oxysterol, 3β3-hyrdoxycholestenoic acid, 3-oxocholestenoic acid, and a 3-oxo-oxysterol; b) administering a treatment to the subject; and c) quantifying, in a second biological sample obtained from the subject after the treatment, the one or more cholesterol, oxidated cholesterol derivative, oxysterol, 3β-hyrdoxycholestenoic acid, 3-oxocholestenoic acid, and/or 3-oxo-oxysterol quantified in step (a). In some embodiments, the first biological sample and the second biological sample are the same type of biological sample. In some embodiment, no change or a decrease in the amount of the oxidated cholesterol derivative, 3-oxocholestenoic acid, or 3-oxo-oxysterol in the second sample, as compared to the first sample, indicates a positive treatment response, or where the amount of the oxidated cholesterol derivative, 3-oxocholestenoic acid, or 3-oxo-oxysterol increases in the second sample as compared to the first sample but the change is less than a change that occurs in a control group of subjects that have the same infection but were not administered treatment. In some embodiment, the biological sample is selected from plasma and/or sputum.

In some embodiments, the level of cholesterol increases or remains the same relative to the subject prior to treatment indicates a positive treatment response. In some embodiments, the oxidated cholesterol derivative is cholestenone. In some embodiments, the methods include determining the ratio value of cholestenone to cholesterol where a decrease or no change in the cholestenone to cholesterol ratio indicates a positive treatment response. In one embodiment, the level of cholestenone is determined from a sputum sample obtained from the subject and the level of cholesterol is determined from a plasma sample obtained from the subject. In another embodiment, the level of cholestenone and the level of cholesterol is determined from a plasma sample obtained from the subject.

In some embodiments, the oxysterol is one or more of 25-hydroxycholesterol, 7α25-hydroxycholesterol, 7α-hydroxycholesterol, 7α27-hydroxycholesterol, and 27-hydroxycholesterol. In some embodiments, the 3-oxo-oxysterol is one or more of 25-hydroxycholestenone, 7α25-hydroxycholestenone, 7α-hydroxycholestenone, 7α27-hydroxycholestenone, and 27-hydroxycholestenone. In some embodiments, the methods include determining the ratio value of 3-oxocholestenoic acid to 3β-hyroxycholestenoic acid where a decrease or no change in the 3-oxocholestenoic acid to 3β-hyroxycholestenoic acid ratio value indicates a positive treatment response.

In some embodiments, the methods include determining the ratio value of 3-oxo-oxysterol to 3β-hyroxy-oxysterol where the ratio value of 3-oxo-oxysterol to 3β-hyroxy-oxysterol is the ratio value of one or more of 25-hydroxy-cholestenone to 25-hydroxycholesterol ratio, 7α25-hydroxycholestenone to α25-hydroxycholesterol ratio, 7α-hydroxycholestenone to 7α-hydroxycholesterol ratio, 7α27-hydroxycholestenone to 7α27-hydroxycholesterol ratio, and 27-hydroxycholestenone to 27-hydroxycholesterol ratio. In some embodiments, a decrease or no change in the ratio value of 3-oxo-oxysterol to 3β-hyroxy-oxysterol indicates a positive treatment response.

In each of the above embodiments, the levels of one or more of cholesterol, an oxidated cholesterol derivative, an oxysterol, a 3β-hyrdoxycholestenoic acid, 3-oxocholestenoic acid, and a 3-oxo-oxysterol can be determined using liquid chromatography-high resolution mass spectrometry.

In some embodiments, the methods include administering an effective amount of at least one antibiotic is selected from the group consisting of rifampicin, isoniazid, pyrazinamide, and ethambutol to the subject. In some embodiments, the methods include administering an effective amount of a corticosteroid to the subject.

In still yet another aspect, the present disclosure provides a method of monitoring a subject having or at risk of having tuberculosis or a non-tuberculous mycobacteria infection, *Rhodococcus* infection or *Nocardia* infection, the method generally include quantifying one or more of cholesterol, an oxidated cholesterol derivative, an oxysterol, 3β-hyrdoxy-cholestenoic acid, 3-oxocholestenoic acid, and a 3-oxo-oxysterol, in a first biological sample obtained from the subject and a second biological sample obtained from the subject, wherein the first biological sample and the second biological sample are the same type of biological sample, and wherein the second biological sample was obtained after the first biological sample; wherein an increase in the amount of the oxidated cholesterol derivative, 3-oxocholestenoic acid, or 3-oxo-oxysterol in the second sample as compared to the first sample indicates an increase in bacterial burden.

In some embodiments, the biological sample is selected from plasma and/or sputum. In some embodiments, the level of cholesterol decrease in the second biological sample indicates increased bacterial burden. In some embodiments, the oxidated cholesterol derivative is cholestenone. In some embodiments, the methods include determining the ratio value of cholestenone to cholesterol where an increase in the cholestenone to cholesterol ratio indicates increased bacterial burden. In one embodiment, the level of cholestenone is determined from a sputum sample obtained from the subject and the level of cholesterol is determined from a plasma sample obtained from the subject. In another embodiment, the level of cholestenone and the level of cholesterol is determined from a plasma sample obtained from the subject.

In some embodiments, the oxysterol is one or more of 25-hydroxycholesterol, 7α25-hydroxycholesterol, 7α-hydroxycholesterol, 7α27-hydroxycholesterol, and 27-hydroxycholesterol. In some embodiments, the 3-oxo-oxysterol is one or more of 25-hydroxycholestenone, 7α25-hydroxycholestenone, 7α-hydroxycholestenone, 7α27-hydroxycholestenone, and 27-hydroxycholestenone. In some embodiments, the methods include determining the ratio value of 3-oxocholestenoic acid to 3β-hyroxycholestenoic acid where an increase in the 3-oxocholestenoic acid to 3β-hyroxycholestenoic acid ratio value indicates an increase in bacterial burden.

In some embodiments, the methods include determining the ratio value of 3-oxo-oxysterol to 3β-hyroxy-oxysterol where the ratio value of 3-oxo-oxysterol to 3β-hyroxy-oxysterol is the ratio value of one or more of 25-hydroxy-cholestenone to 25-hydroxycholesterol ratio, 7α25-hydroxycholestenone to α25-hydroxycholesterol ratio, 7α-hydroxycholestenone to 7α-hydroxycholesterol ratio, 7α27-hydroxycholestenone to 7α27-hydroxycholesterol ratio, and 27-hydroxycholestenone to 27-hydroxycholesterol ratio. In some embodiments, an increase in the ratio value of 3-oxo-oxysterol to 3β-hyroxy-oxysterol indicates an increase in bacterial burden.

BRIEF DESCRIPTION OF THE FIGURES

FIG. 1A is a schematic showing murine BMDMs were incubated with Mtb H37Rv at MOI 5 for 4 hours after which extracellular bacteria were removed. Infected macrophages were harvested 3 and 24 hpi for metabolomics analyses. At each time point, uninfected cells were used as controls. FIG. 1B is a graph showing a biochemical importance plot indicating the top 30 metabolites that differentiate between uninfected and Mtb-infected macrophages. The mean decrease accuracy quantifies the importance of a metabolite to the prediction accuracy of the model. A higher value shows that the metabolite has more importance to group separation. The color of each molecule indicates the metabolic pathway with which it is associated. This plot is derived from Random Forest analysis of the metabolomics profile of 507 biochemicals obtained from 19 samples. See methods for additional details.

FIG. 3A shows chemical structures of cholesterol and cholestenone showing A-D rings (red text). The 3-hydroxyl group of cholesterol is dehydrogenated to a keto moiety in the A ring in cholestenone (highlighted in green). FIG. 3B shows cholestenone was quantified from BMDMs infected with Mtb at MOI 1, 5 and 10, at 3, 24, 72 and 120 hpi. Uninfected (UI) cells or those infected with heat-killed Mtb (HK) were used as controls. Plot shows average of two independent experiments. *$p=0.03$, **$p=0.007$ for 120 h calculated using Mann-Whitney test. FIG. 3C shows cholestenone levels in PMA-differentiated THP-1 macrophages that were uninfected or Mtb-infected at MOI 10, 72 hpi. FIG. 3D shows growth of Mtb was compared in minimal medium supplemented with either a vehicle control, 100

μg/mL 25-HC, or 100 μg/mL cholesterol. Plot shows values from one experiment representative of three independent experiments. FIG. 3E shows cholestenone abundance and FIG. 3F corresponding Mtb CFU in IFNγ-activated and naïve BMDMs that were uninfected or Mtb-infected at MOI 10 at the indicated time points. (FIG. 3G, FIG. 3H) The direct effect of cholestenone on Mtb growth was assessed in culture medium using absorbance measurements FIG. 3G and CFU FIG. 3H. (FIG. 3C, FIG. 3E-FIG. 3F) Plots show mean+/−s.e.m. from at least three independent experiments. p=0.007, p<0.0001 calculated using Student's t-test (FIG. 3C), and one-way ANOVA with Tukey's multiple comparisons test (FIG. 3E, FIG. 3F). (FIG. 3G-FIG. 3H) Plots show average of two independent experiments. (FIG. 3C, FIG. 3**E) The dotted line on the y-axis represents the limit of detection accuracy as determined by the standard curve. For all macrophage experiments, one million cells were infected, and the samples were extracted in 500 μL of 80% methanol solution containing 0.1 μg internal standard.

FIG. 4A-FIG. 4B show growth of H37Rv, Δhsd, Δhsd att::pCH89 (ΔhsdpCH89) and ΔchoD in FIG. 4A minimal media and FIG. 4B 7H9 supplemented with OADC. Cultures supplemented with cholesterol are indicated by closed symbols, while open symbols represent cultures with the vehicle control. Cholesterol abundance in the cultures is represented with the dotted lines. FIG. 4C show cholestenone abundance measured during growth of H37Rv, Δhsd, ΔhsdpCH89 and ΔchoD in 7H9 supplemented with OADC and cholesterol (100 μg/mL). FIG. 4D show growth of H37Rv, Δhsd, ΔhsdpCH89 and ΔchoD in minimal media supplemented with cholesterol, expressed as the ratio of OD600 nm for each strain normalized to H37Rv. Plot shows the mean and s.e.m from three independent experiments, *p<0.05 indicates significance between H37Rv and Δhsd and was done using Student's t-test. FIG. 4E-FIG. 4F show cholestenone abundance at 72 hpi in FIG. 4E BMDMs and FIG. 4F PMA-differentiated THP-1 macrophages infected with wild type Mtb, Δhsd, H37Rv att::pCH89 (H37RvpCH89), or ΔhsdpCH89. FIG. 4G shows cholestenone abundance in BMDMs infected with *M. abscessus* at MOI 1, 24 hpi. FIG. 4A-FIG. 4C are graphs are representative of three independent experiments. FIG. 4E-FIG. 4G data shows FIG. 4E mean+/−s.d. from at least two independent experiments, and FIG. 4F-FIG. 4G s.e.m. from three independent experiments. FIG. 4E-FIG. 4G *p=0.01, p≤0.004, p<0.0001 calculated using FIG. 4E-FIG. 4F one-way ANOVA with Tukey's multiple comparisons test and FIG. 4G Student's t-test. UI=uninfected. FIG. 4C, FIG. 4E-FIG. 4**F the dotted line on the y-axis represents the limit of detection accuracy as determined by the standard curve. For all macrophage experiments, one million cells were infected, and the samples were extracted in 500 μL of 80% methanol solution containing 0.1 μg internal standard.

FIG. 5A shows sputum cholestenone level and FIG. 5B corresponding ROC curve. FIG. 5C shows plasma cholestenone level and FIG. 5D corresponding ROC curve. FIG. 5E shows cholesterol level in sputum and FIG. 5F corresponding ROC curves. FIG. 5G shows cholesterol level in plasma and FIG. 5H corresponding ROC curves. Statistical analyses were done using the Mann-Whitney test for sputum samples and Student's t-tests for plasma samples. ns=not significant, *p<0.05, p<0.01, *p<0.001, ****p<0.0001.

FIG. 6C Ratio of plasma cholestenone and plasma cholesterol in control and TB patients of both countries, and the FIG. 6D corresponding ROC curve. FIG. 6A, FIG. 6C show the ratios were determined on a per-subject basis and were multiplied by a factor $10^6$ for clarity. Statistical analyses were done using the Mann-Whitney test for sputum samples and Student's t-tests for plasma samples. ns=not significant, *p<0.05, p<0.01, *p<0.001, ****p<0.0001.

DETAILED DESCRIPTION

Figure 1A:
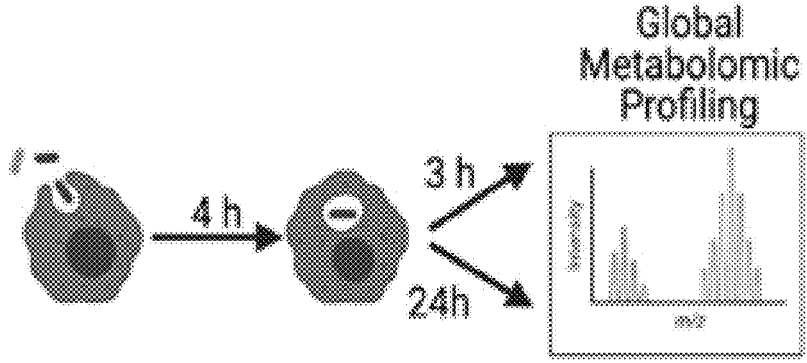
FIG. 1A and FIG. 1B show that global metabolomic profiling identifies metabolites that discriminate Mtb infected from uninfected macrophages.

Among the various aspects of the disclosure is the provision of methods to detect and optionally quantify one or more of cholesterol, an oxidated cholesterol derivative (e.g., cholestenone (4-cholesten-3-one), an oxysterol, and/or 3-oxo-derivative of an oxysterol (e.g., 3-oxocholestenoic acid) in biological sample and use of the methods to detect and optionally measure levels of one or more of cholesterol, an oxidated cholesterol derivative, an oxysterol, and/or 3-oxo-oxysterol derivative biomarkers indicative of infection. As described in greater detail herein, it has been discovered that *Mycobacterium tuberculosis* (Mtb)-host co-metabolites of cholesterol are promising TB biomarkers. These co-metabolites are useful for sputum-based tests to replace smear microscopy, a non-sputum-based tests capable of detecting all forms of TB, and/or tests for monitoring TB treatment success. The accumulation of cholestenone and 3-oxocholestenoic acid during infection depends on the enzyme 3β-hydroxysteroid dehydrogenase (3β-Hsd) and correlated with pathogen burden. These co-metabolites can be used to guide treatment decisions in tuberculosis, leprosy, and infection with non-tuberculous mycobacteria or other rare infections caused by bacteria such as *Nocardia* and *Rhodococcus*, which also oxidize cholesterol to cholestenone.

I. Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

The term "about," as used herein, refers to variation of in the numerical quantity that can occur, for example, through typical measuring techniques and equipment, with respect to any quantifiable variable, including, but not limited to, mass, volume, time, distance, and amount. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5%, but can also be ±4%, 3%, 2%, 1%, etc. Whether or not modified by the term "about," the claims include equivalents to the quantities.

In this disclosure, "comprises," "comprising," "containing," and "having" and the like can have the meaning ascribed to them in U.S. Patent Law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

As used herein, a "biological sample" refers to a sample of tissue, cells, or fluid isolated from a subject, including but not limited to, for example, blood, buffy coat, plasma, serum, immune cells (e.g., macrophages), sputa, fecal matter, urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components. As used herein, the term "blood sample" refers to a biological sample derived from blood, preferably peripheral (or circulating) blood. The blood sample can be whole blood, plasma or serum, although plasma is typically preferred.

The term "subject" refers to a human, or to a non-human animal.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

"Differentially expressed" refers to differences in the quantity and/or the frequency of a biomarker present in a sample taken from subjects having, for example, tuberculosis as compared to a control subject or non-infected subject. For example, a biomarker can be a metabolite which is present at an elevated level or at a decreased level in samples of subjects with tuberculosis compared to samples of control subjects.

II. Methods for Detecting Cholesterol Metabolites in a Biological Sample

In one aspect, the present disclosure provides a method for detecting a cholesterol metabolite in a biological sample. The method comprises providing a biological sample and detecting one to a plurality of the cholesterol metabolites.

(a) Providinq a Biological Sample

Suitable biological samples include a sputum sample and/or a plasma sample obtained from a subject. Sputum and/or plasma contain a plurality of differentially expressed cholesterol metabolites, as detailed in the Examples.

The size of the biological sample used may vary depending upon the sample type, the health status of the subject from whom the sample was obtained, and the analytes in addition to cholesterol metabolites to be analyzed (e.g., itaconate, methylsuccinate, methylcitrate, 2-aminoadipate, propionylcarnitine, etc.). Biological sample volumes may be about 0.01 mL to about 5 mL, or about 0.05 mL to about 5 mL. In a specific example, the size of the sample may be about 0.05 mL to about 1 mL. Plasma sample volumes may be about 0.01 mL to about 20 mL, or about 0.1 mL to about 20 mL. In a specific example, the size of the sample may be about 1 mL to about 20 mL blood.

In some embodiments, the subject is a human. A human subject may be waiting for medical care or treatment, may be under medical care or treatment, or may have received medical care or treatment. In various embodiments, a human subject may be a healthy subject, a subject at risk of developing a bacterial infection (e.g., *Mycobacterium tuberculosis*), a subject with signs and/or symptoms of a bacterial infection, or a subject diagnosed with a bacterial infection. The bacterial infection may be tuberculosis, leprosy, an infection with non-tuberculous mycobacteria or other rare infections caused by bacteria such as *Nocardia* and *Rhodococcus*. A healthy subject, sometimes referred to as a "control subject" or a "healthy control", minimally has no clinical signs or symptoms of infection and may also be "negative" for other clinical indicators of infection such as negative by sputum smear microscopy and culture, Xpert and QuantiFERON assay.

In other embodiments, the subject is a non-human animal (e.g., a laboratory animal, cattle, elephant). In a further embodiment, the subject is a laboratory animal model of infection.

A biological sample can be obtained from a subject by conventional techniques. For example, blood can be obtained by venipuncture, and solid tissue samples can be obtained by surgical techniques according to methods well known in the art. Multiple samples contemporaneously collected from a subject may be pooled to create "a sample". Once collected, samples may have been processed according to methods known in the art (e.g., centrifugation to remove whole cells and cellular debris; use of additives designed to stabilize and preserve the specimen prior to analytical testing; etc.). Samples may be used immediately or may be frozen and stored indefinitely.

Prior to use in the methods disclosed herein, a biological sample may also have been modified, if needed or desired, to include protease inhibitors, internal standards, detergent(s) and chaotropic agent(s), to deplete other analytes (e.g., proteins, peptides, metabolites, etc.), or any combination thereof.

The term "deplete" means to diminish in quantity or number. Accordingly, a sample depleted of a protein may have any amount of the protein that is measurably less than the amount in the original sample, including no amount of the protein. As a non-limiting example, protein(s) may be depleted from a sample by ultrafiltration or protein precipitation with an acid, an organic solvent or a salt. Generally speaking, these methods are used to reliably reduce high abundance and high molecular weight proteins. In a specific example, proteins may be depleted from a sample by precipitation. Briefly, precipitation comprises adding a precipitating agent to a sample and thoroughly mixing, incubating the sample with precipitating agent to precipitate proteins, and separating the precipitated proteins by centrifugation or filtration. The resulting supernatant may then be used in downstream applications. The amount of the reagent needed may be experimentally determined by methods known in the art. Suitable precipitating agents include perchloric acid, trichloroacetic acid, acetonitrile, methanol, and the like. In an exemplary embodiment, proteins are depleted from a sample by methanol.

(b) Enrichinq for One to a Plurality of Metabolites in the Biological Sample

The term "enrich" means to increase in quantity or number. Biological samples contain a plurality of cholesterol and sterols. Accordingly, "enriching for one to a plurality of cholesterol, hydroxysterols, cholestenoic acids, and their 3-oxo analogues in the biological sample" means measurably increasing the amount of the cholesterol, hydroxysterols, cholestenoic acids, and their 3-oxo analogues, per volume of sample as compared to the starting sample (i.e., the biological sample). In some examples, enrichment may be at least about 5-fold. In some examples, enrichment may be about 5-fold to about 1000-fold. For instance, enrichment may be at least about 5-fold, about 10-fold, about 20-fold, about 50-fold, about 100-fold, about 200-fold, about 300-fold, about 400-fold, about 500-fold, about 600-fold, about 700-fold, about 800-fold, about 900-fold, about 1000-fold, or more.

Methods of the present disclosure may enrich for the metabolites of the present disclosure from the biological sample (e.g., affinity purification, solid phase extraction, etc.) and/or by removing other sterols from the biological sample (e.g., affinity depletion, solid phase extraction etc.).

An internal standard (abbreviated herein as "ISTD") may be used to account for variability throughout enrichment and optionally to calculate an absolute concentration. Generally, an internal standard is added before significant sample processing, and it can be added more than once if needed. One or more 3β-hydroxysterols, 3-oxosterols, and/or cholestenone may be used. For instance, in embodiments with sequential isolation of multiple metabolites, it may be advantageous to use a number of internal standards equal to the number of isolation steps, wherein each internal standard is a different metabolite, such that each isolation step will only isolate a single internal standard. In some embodiments, each internal standard may be a different, stable, isotope-labeled metabolite corresponding to a metabolite of interest to be detected by MS. Typically, internal standards are detectably labeled, so as to differentiate the metabolite standard from endogenous metabolite, but without affecting the chemical properties relied upon for separation. In some embodiments, an internal standard is an isotope-labeled internal metabolite standard. Suitable isotope-labeled internal metabolite standards have a heavy isotope label incorporated. Generally speaking, the isotope-labeled metabolite should increase the mass of the metabolite without affecting its chemical properties, and the mass shift resulting from the presence of the isotope labels must be sufficient to allow the mass spectrometry method to distinguish the internal standard (IS) from endogenous metabolite signals. As shown herein, suitable heavy isotope labels include, but are not limited to $^{2}H$, $^{13}C$, and $^{15}N$.

Metabolites can be detected, and optionally quantified, by mass spectrometry, as further detailed below or in the Examples, or by other methods known in the art, including but not limited to an immunoassay, a multiplexed assay (such as xMAP technology by Luminex), a single molecule array assay (such as Simoa® bead technology), a proximity ligation assay (such as DuoLink® by Sigma Aldrich), colorometric/fluorometric enzymatic assay, or the like.

In some embodiments, metabolites are detected, and optionally quantified, in an enriched sample by mass spectrometry. Briefly, detection by mass spectrometry comprises solid phase extraction and performing liquid chromatography-mass spectrometry (LC/MS) of the sample to detect at least one metabolite of the disclosure. In any of the methods disclosed herein, the amount any metabolite may also be quantified (e.g., from the height or integration of the peak in a MS analysis corresponding to the appropriate metabolite).

Metabolites may be separated by a liquid chromatography system interfaced with a high-resolution mass spectrometer. Suitable LC-MS systems may comprise a <1.0 mm ID column and use a flow rate less than about 100 μl/min.

Tandem mass spectrometry may be used to improve resolution, as is known in the art, or technology may improve to achieve the resolution of tandem mass spectrometry with a single mass analyzer. Suitable types of mass spectrometers are known in the art. These include, but are not limited to, quadrupole, time-of-flight, ion trap and Orbitrap, as well as hybrid mass spectrometers that combine different types of mass analyzers into one architecture (e.g., Orbitrap Fusion™ Tribrid™ Mass Spectrometer, Orbitrap Fusion™ Lumos™ Mass Spectrometer, Orbitrap Tribrid™ Eclipse™ Mass Spectrometer, Q Exactive Mass Spectrometer, each from ThermoFisher Scientific). Suitable mass spectrometry protocols may be developed by optimizing the number of ions collected prior to analysis (e.g., (AGC setting using an orbitrap) and/or injection time. In an exemplary embodiment, a mass spectrometry protocol outlined in the Examples is used.

Metabolites analyzed by the MS may be quantified by methods known in the art. Generally speaking, a known amount of an internal standard is added to a sample. The sample is then digested and analyzed by LC-MS. Extracted ion chromatograms are generated for the native peptide and the internal standard. Using peak ratios (e.g., 14N/15N), the quantity of native peptide is calculated.

III. Methods for Detecting a Biomarker and Use Thereof

In another aspect, the present disclosure provides a method for detecting, and optionally quantifying, a metabolite (e.g., cholesterol, an oxidated cholesterol derivative (e.g., cholestenone (4-cholesten-3-one)), an oxysterol, 3β-hydroxycholestenoic acid, 3-oxocholestenoic acid, and/or 3-oxo-derivative of an oxysterol (e.g., 3-oxocholestenoic acid)) biomarker in a sample obtained from a subject. The method comprises detecting and optionally quantifying a metabolite according to a method of Section II, wherein the biological sample is a sample obtained from a subject having or at risk of having a bacterial infection, and wherein the biomarker is one or more of cholesterol, cholestenone, 3-oxocholestenoic acid, 24S-hydroxycholesterol, 7β-hydroxycholesterol, 24S,25-epoxycholesterol, 3β-hydroxycholestenoic acid, 3β-hydroxycholenoic acid, 27-hydroxycholesterol, 7α,27-dihydroxycholesterol, 7α-hydroxycholesterol, 7α,25-dihydroxycholesterol, 25-hydroxycholesterol, 25-hydroxycholestenone, 7α,25-dihydroxycholestenone, 7α-hydroxycholestenone, 7α,27-dihydroxycholestenone, and 27-hydroxycholestenone, a ratio of a first metabolite to a second metabolite, for example, a ratio of ratio of 3-oxo-oxysterol/3β-hydroxy-derivatives, an enriched population of metabolite, or a ratio of a first population of enriched metabolite and a second population of enriched metabolite. In some embodiment, the bacterial infection may be tuberculosis, leprosy, an infection with non-tuberculous mycobacteria or other rare infections caused by bacteria such as *Nocardia* and *Rhodococcus*. A healthy subject, sometimes referred to as a "control subject" or a "healthy control", minimally has no clinical signs or symptoms of infection and may also be "negative" for other clinical indicators of infection such as negative by sputum smear microscopy and culture, Xpert and QuantiFERON assay.

In some embodiments, the biomarker may be a population of metabolites selected from the group consisting of cholesterol, cholestenone, 3-oxocholestenoic acid, 24S-hydroxycholesterol, 7β-hydroxycholesterol, 24S,25-epoxycholesterol, 3β-hydroxycholestenoic acid, 3β-hydroxycholenoic acid, 27-hydroxycholesterol, 7α,27-dihydroxycholesterol, 7α-hydroxycholesterol, 7α,25-dihydroxycholesterol, 25-hydroxycholesterol, 25-hydroxycholestenone, 7α,25-dihydroxycholestenone, 7α-hydroxycholestenone, 7α,27-dihydroxycholestenone, 27-hydroxycholestenone, or any combination thereof.

In further embodiments, the biomarker may be a ratio of two biomarkers described above. As non-limiting examples, the biomarker may be a ratio of two 3β-hydroxycholesterols biomarkers, or a ratio of two 3-oxo-oxysterol biomarkers, or more preferably a ratio of one 3-oxo-oxysterol biomarker and one 3β-hydroxy-oxysterol biomarker, preferably the ratio is between the 3β-hydroxy-oxysterol and its corresponding (i.e., converted form) 3-oxo-oxysterol (e.g., 3-oxocholestenoic acid/3β-hydroxycholestenoic acid). In still further embodiments, the biomarker may be a ratio of cholestenone to cholesterol. In some embodiments, one metabolite is detected from a serum sample and the other metabolite is detected from a sputum sample of the same subject. In other embodiments, the metabolites are detected from the same sample type from the same subject. Other mathematical operations, and the use of more than two biomarkers, are also contemplated. For example, when a first and second biological sample are analyzed where the second sample is obtained a period of time after the first (e.g., days, weeks, months, years) the rate of change of a biomarker may be used.

In one example, the method comprises (a) providing a biological sample obtained from the subject, wherein the biological sample is a serum sample or a sputum sample, (b) enriching for one to a plurality of metabolites in the biological sample; and (c) detecting and optionally quantifying one to a plurality of metabolites, wherein the metabolite is selected from the group consisting of cholesterol, cholestenone, 3-oxocholestenoic acid, 24S-hydroxycholesterol, 7β-hydroxycholesterol, 24S,25-epoxycholesterol, 3β-hydroxycholestenoic acid, 3β-hydroxycholenoic acid, 27-hydroxycholesterol, 7α,27-dihydroxycholesterol, 7α-hydroxycholesterol, 7α,25-dihydroxycholesterol, 25-hydroxycholesterol, 25-hydroxycholestenone, 7α,25-dihydroxycholestenone, 7α-hydroxycholestenone, 7α,27-dihydroxycholestenone, 27-hydroxycholestenone, a ratio of one 3-oxo-oxysterol to 3β-hydroxy-oxysterol (e.g., 3-oxocholestenoic acid/3β-hydroxycholestenoic acid), a ratio of cholestenone to cholesterol, or any combination thereof.

Detection and quantification of the biomarker may be used for a number of purposes. Non-limiting examples include diagnosing a bacterial infection, diagnosing a disease or condition characterized by a bacterial infection, monitoring/measuring the development or progression of a bacterial infection, treating a subject with a bacterial infection, determining/measuring the efficacy of a given treatment, and the like.

Accordingly, in another aspect, the method comprises detecting and quantifying the level of a biomarker, as described in any of the embodiments above, and determining if the level is elevated, reduced, or the same in comparison to its level in control subjects who are healthy controls. In another aspect, the method comprises detecting and quantifying the level of a biomarker, as described in any of the embodiments above, and determining if the level is elevated, reduced, or the same in comparison to its level in control subjects who are negative for one or more additional clinical sign or symptom of a bacterial infection. Clinical tests for evaluating bacterial infection are known in the art and also discussed above In some embodiments, a subject may be diagnosed as having a bacterial infection when the level of the biomarker significantly deviates from the mean in the control subjects. "Significantly deviates from the mean" refers to values that are at least 1 standard deviation, preferably at least 1.3 standard deviations, more preferably at least 1.5 standard deviations or even more preferably at least 2 standard deviations, above or below the mean (e.g., 1σ, 1.1σ, 1.2σ, 1.3σ. 1.4σ, 1.5σ, etc., where σ is the standard deviation defined by the normal distribution measured in a control population). In addition to using a threshold (e.g., at least 1 standard deviation above or below the mean), in some embodiments the extent of change above or below the mean may be used to diagnose a subject.

Biomarker data may be analyzed by a variety of methods to identify biomarkers and determine the statistical significance of differences in observed levels of expression of the biomarkers between test and reference expression profiles in order to evaluate whether a subject has an infectious disease. In certain embodiments, subject data is analyzed by one or more methods including, but not limited to, multivariate linear discriminant analysis (LDA), receiver operating characteristic (ROC) analysis, principal component analysis (PCA), ensemble data mining methods, significance analysis of microarrays (SAM), cell specific significance analysis of microarrays (csSAM), spanning-tree progression analysis of density-normalized events (SPADE), and multi-dimensional protein identification technology (MUDPIT) analysis. (See, e.g., Hilbe (2009) Logistic Regression Models, Chapman & Hall/CRC Press; McLachlan (2004) Discriminant Analysis and Statistical Pattern Recognition. Wiley Interscience; Zweig et al. (1993) Clin. Chem. 39:561-577; Pepe (2003) The statistical evaluation of medical tests for classification and prediction, New York, N.Y.: Oxford; Sing et al. (2005) Bioinformatics 21:3940-3941; Tusher et al. (2001) Proc. Natl. Acad. Sci. U.S.A. 98:5116-5121; Oza (2006) Ensemble data mining, NASA Ames Research Center, Moffett Field, Calif., USA; English et al. (2009) J. Biomed. Inform. 42(2):287-295; Zhang (2007) Bioinformatics 8: 230; Shen-Orr et al. (2010) Journal of Immunology 184: 144-130; Qiu et al. (2011) Nat. Biotechnol. 29(10):886-891; Ru et al. (2006) J. Chromatogr. A. 1111(2):166-174, Jolliffe Principal Component Analysis (Springer Series in Statistics, 2 nd edition, Springer, N Y, 2002), Koren et al. (2004) IEEE Trans Vis Comput Graph 10:459-470; herein incorporated by reference in their entireties.)

In another aspect, the method comprises detecting and quantifying the level of a biomarker, as described in any of the embodiments above, in a first biological sample obtained from the subject and a second biological sample obtained from the subject, wherein the first biological sample and the second biological sample are both the same sample, and wherein the second biological sample was obtained after the first biological sample.

In another aspect, the method comprises detecting and quantifying the level of a biomarker, as described in any of the embodiments above, in a first biological sample obtained from the subject and a second biological sample obtained from the subject, wherein the first biological sample and the second biological sample are both the same type of biological sample, and wherein the second biological sample was obtained after the first biological sample. An increase in the level of biomarker in the second sample as compared to the first sample indicates an increase in bacterial burden. In some embodiments, the rate of change in the levels of the biomarker between the first and subsequent samples is used to determine the stage of disease and/or extent of infection. Accordingly, such methods may be used to monitor a subject has an active infection or is at risk of having a bacterial infection.

In some embodiments, one or more of the above methods may be used in combination with one or more disease biomarker known in the art to diagnose, stage, and/or treat specific bacterial infections.

In another aspect, the method comprises (a) detecting and quantifying the level of a biomarker, as described in any of the embodiments above, in a first biological sample obtained from the subject, a biomarker as described herein; (b) administering a treatment to the subject; and (c) detecting and quantifying, in a second biological sample obtained from the subject after the treatment, the biomarker quantified in step (a); wherein the first biological sample and the second biological sample are both the same type of biological sample. Either no change in the level of the biomarker, or a decrease in the level of the biomarker, in the second sample as compared to the first sample indicates a positive treatment response. In addition, an increase in the level of the biomarker in the second sample as compared to the first sample may also indicate a positive treatment response when the increase is less than an increase that occurs in a control group of subjects that have active infection but were not administered treatment. Preferably the control subjects in such an embodiment have an infection due to the same disease process or pathogen type. Accordingly, such methods may be used to measure a treatment response in a subject having or at risk of having neuronal damage.

In another aspect, the present disclosure comprises treating a subject diagnosed with a bacterial infection. The method comprises (a) quantifying, in a sample obtained from the subject, a biomarker as described herein; and (b)

administering to the subject a pharmaceutical composition to decrease or stabilize the amount of the biomarker measured in step (a).

Antibiotics that may be used in treating an infection, such as tuberculosis include, but are not limited to, ethambutol, isoniazid, pyrazinamide, rifabutin, rifampin, rifapentine, amikacin, capreomycin, cycloserine, ethionamide, levofloxacin, moxifloxacin, para-aminosalicylic acid, and streptomycin. Typically, several antibiotics are administered simultaneously to treat active tuberculosis, whereas a single antibiotic is administered to treat latent tuberculosis. Treatment may continue for at least a month or several months, up to one or two years, or longer, depending on whether the tuberculosis infection is active or latent. Longer treatment is generally required for severe tuberculosis infection, particularly if the infection becomes antibiotic resistant. Latent tuberculosis may be effectively treated in less time, typically 4 to 12 months, to prevent tuberculosis infection from becoming active. Subjects, whose infection is antibiotic resistant, may be screened to determine antibiotic sensitivity in order to identify antibiotics that will eradicate the tuberculosis infection. In addition, corticosteroid medicines also may be administered to reduce inflammation caused by active tuberculosis.

IV. Compositions

In another aspect, the present disclosure also provides compositions comprising a biomarker of Section III and an internal standard.

In yet another aspect, the disclosure provides compositions for diagnosing tuberculosis, wherein the compositions can be used to detect the biomarkers of the present disclosure. For example, the composition can be used to detect any one or more of the biomarkers described herein, which are differentially expressed in samples of a tuberculosis patient and healthy or non-infected subjects. The composition may include one or more agents for detection of biomarkers, a container for holding a biological sample isolated from a human subject suspected of having tuberculosis; and printed instructions for reacting agents with the biological sample or a portion of the biological sample to detect the presence or amount of at least one tuberculosis biomarker in the biological sample. The agents may be packaged in separate containers. The composition may further comprise one or more control reference samples and reagents for performing mass-spec analysis.

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense.

Example 1-*Mycobacterium tuberculosis*-Host Co-Metabolite Present in Human Tuberculosis Infection As a central aspect of its pathogenesis, Mtb grows in macrophages, and host and microbe influence each other's metabolism. Previous work investigated immuno-metabolic dynamics of the host during Mtb infection and showed that Mtb induces miR-33 to control host pathways critical for its intracellular survival including lipid metabolism and autophagy. It was also shown that intracellular growth of Mtb depends on macrophage fatty acid catabolism and that inhibiting host fatty acid catabolism enhances immune effector functions against Mtb. In the present example, an unbiased metabolomics analysis was performed to explore perturbations in metabolic pathways during Mtb infection. It was discovered that Mtb-infected macrophages preferentially utilize glucose, channel TCA cycle intermediates for itaconate production, and induce perturbations in redox homeostasis. As previous reports have shown, such metabolic changes support host antimicrobial functions by allowing rapid ATP and NADPH production, enhancing oxidative stress and inflammation, and providing raw materials for plasma membrane synthesis and protein export. In addition to these immuno-metabolic changes, a prominent metabolic signature of cholesterol metabolism was found, with cholestenone (4-cholesten-3-one) the second most discriminating metabolite between infected and uninfected cells.

Host cholesterol can serve as a carbon source that feeds mycobacterial central metabolism and the biosynthesis of methyl-branched fatty acids. Mtb induces the formation of lipid-droplet-filled or foamy macrophages. In these foamy macrophages, Mtb-containing phagosomes are in close approximation to host lipid droplets. Mtb also grows extracellularly in the lipid-rich caseum of necrotic granulomas. Cholesterol utilization by Mtb has been linked to dormancy and persistence. Mtb oxidizes host cholesterol to cholestenone, which is thought to be a necessary intermediate in cholesterol degradation. Mtb is able to completely degrade cholesterol through a process involving enzymes of the KstR1 regulon, which degrade the side chain and A/B ring, and the KstR2 regulon, which metabolize the C/D ring. Humans do not have a similar pathway to degrade cholesterol. Instead, cholesterol serves as a critical component of cellular membranes and is used for biosynthesis of bile acids, steroid hormones, and vitamin D. This raises the possibility that Mtb-specific cholesterol metabolites might be involved in pathogenesis and serve as unique biomarkers of infection. Using clinical samples from two cohorts of patients, recruited from Peru and Vietnam, the present example establishes cholestenone as a biomarker of TB infection.

Methods

Bacterial strains: *M. tuberculosis* (H37Rv strain) was grown aerobically at 37° C. in Middlebrook 7H9 broth with 0.05% Tyloxapol, 0.2% glycerol, and OADC (oleic acid-albumin-dextrose-catalase; Cat. No. 212351; BD Biosciences). When required, antibiotics were added in the culture media with the following concentrations: 25 μg/mL kanamycin, 50 μg/mL hygromycin, and 25 μg/mL zeocin. The strains used in this study and details for their construction can be found in the Supplemental Methods. The mutant strains are isogenic derivatives of H37Rv, built using ORBIT (Oligonucleotide-mediated Recombineering followed by Bxb1 Integrase Targeting) mediated mutagenesis and confirmed by PCR analysis. The Δhsd mutant was complemented with an integrating plasmid (pCH89), containing the full Hsd operon (Rv1106c-Rv1109c). PDIM production by the strains was confirmed by mass spectrometry.

Cell culture: Bone marrow-derived macrophages (BMDMs) were obtained from 8-12 week old C57Bl/6 mice that were obtained from The Jackson Laboratory. Bone marrow was flushed from the femurs and tibia of mice as described previously. BMDMs and THP-1 cells (American Type Tissue Collection) were maintained as previously described. To promote macrophage differentiation, THP-1 cells were treated with 100 nM phorbol myristate acetate (PMA; Sigma) for 24 h before infection. BMDMs were activated with IFN-γ (Thermofisher Cat. No. PMC4031) at a concentration of 10 units/mL.

Global metabolomics profiling: For global metabolic profiling, BMDMs isolated from eight C57Bl/6 mice (aged 8-12 weeks obtained from The Jackson Laboratory) were pooled and used for four experimental groups—uninfected and Mtb-infected at 3 and 24 hour time points. Each group had five replicates (N=20 samples total). 15 million murine BMDMs were infected with H37Rv at an MOI of 5 for 4 hours. Cells were then washed to remove extracellular bacteria and maintained in culture medium for 3 or 24 hours. At the respective time points, BMDMs were washed twice with sterile Hank's Balanced Salt Solution (HBSS, Gibco), and metabolites were extracted in 80% methanol (Sigma) in water (Corning) containing pre-measured internal standards provided by Metabolon. The samples were stored at −80° C. prior to shipping to Metabolon Inc., NC for further processing and analyses. At Metabolon, the samples were prepared using the automated MicroLab STAR® system from Hamilton Company. After addition of recovery standards and protein removal, the extracts were divided into fractions for analysis by: two separate reverse phase (RP)/UPLC-MS/MS with positive ion mode electrospray ionization (ESI), RP/UPLC-MS/MS with negative ion mode (ESI), and HILIC/UPLC-MS/MS with negative ion mode ESI. All methods utilized a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. Raw data was extracted, peak-identified, and QC processed using Metabolon's hardware and software that are built on a web-service platform using Microsoft's .NET technologies. Metabolon maintains a library based on authenticated standards that contain the retention time/index (RI), mass to charge ratio, and chromatographic data (including MS/MS spectral data) on all molecules present in the library. To distinguish biochemicals, their identifications were based on three criteria: retention index within a narrow RI window of the proposed identification, accurate mass match to the library+/−10 ppm, and the MS/MS forward and reverse scores between the experimental data and authentic standards. Peaks were quantified using area-under-the-curve. Missing values were imputed with the minimum observed value for each compound. To determine scaled intensity, the raw area counts for each biochemical were rescaled to set the median equal to 1. Statistical analyses were conducted on the scaled and imputed data.

Random forest analysis: Random forest represents a supervised classification technique based on biochemical profile of the dataset. Random forest analysis was done in RStudio using the package 'randomForest' with sampsize=rep(m1, 11) and ntree=50,000 where m1 is half the smallest group in the random forest, 11 is the number of groups, and ntree is the number of trees. To build the random forest, all 507 metabolites were included from 19 out of 20 samples. The analysis misidentified one infected sample resulting in an out-of-bag (OOB) error of 1/19 and predictive accuracy of 95%.

In vitro growth assays: To assess Mtb growth in defined carbon sources, the strains were grown in minimal media 0.5 g/L asparagine, 1 g/L KH2PO4, 2.5 g/L Na2HPO4, 5 mg/L ferric ammonium citrate, 0.5 g/L $MgSO_4.7H_2O$, 0.5 mg/L $CaCl_2$), and 0.1 mg/L $ZnSO_4$,). As needed, carbon sources were provided either through 0.1% glycerol (vol/vol) or 0.01% cholesterol (wt/vol). Cholesterol was added using a 100× stock solution prepared in tyloxapol:ethanol (1:1). Growth was monitored using a cell density meter and normalized to the optical density of the culture medium. Throughout the growth curves, bacterial samples were withdrawn for cholesterol and cholestenone quantification. For cholesterol quantification, at defined time points, culture samples were frozen at −80° C., until they were processed together for total cholesterol (free cholesterol+esterified cholesterol) quantification using the Amplex Red Cholesterol Assay Kit (Invitrogen). For cholestenone analysis, the bacterial culture samples were centrifugated, washed twice in PBS, and the pellets stored at −80° C. until they were processed for mass spectrometry. For the investigation of cholestenone bactericidal activity on *M. tuberculosis*, cholestenone was prepared in ethanol as 100× stock solutions to achieve indicated final concentrations.

Chemicals and reagents: The following compounds were used as internal standards or reference compounds: (±)-2 methyl-d3-succinic-2,3,3-$d_3$ acid (Cat. No. M329046; Toronto Research Chemicals (TRC; Toronto, Canada), methylmalonic acid-$d_3$ (Cat. No. M318862; TRC), 2-methylcitric acid-$d_3$ (Cat. No. M265082; TRC), itaconic acid-$^{13}C5$ (Cat. No. 1931004; TRC), 4-cholesten-3-one-2,2,4,6,6-$d_5$ (Cat. No. D-5467; CDN isotopes; Pointe-Claire, Canada) 4-cholesten-3-one (Cat. No. 188174; Sigma-Aldrich), itaconic acid (Cat. No. 129204; Sigma-Aldrich), methylcitric acid (Cat. No. M265080; TRC), methylmalonic acid (Cat. No. M318862; TRC), and methylsuccinic acid (Cat. No. M329045: TRC). All HPLC grade solvents were purchased from Sigma (St. Louis, MO).

Mass spectrometry identification of metabolites: Liquid chromatography-tandem mass spectrometry (LC-MS/MS) methods were used to analyze metabolites extracted from samples derived from either bacterial pellets, infected cells or human clinical samples obtained from FIND. Samples were extracted with 80% methanol, and the appropriate internal standards were included in the extraction buffer at final concentrations: 0.20 μg/mL 4-cholesten-3-one-2,2,4,6,6-d5, 0.1 μg/mL (±)-2-methyl-succinic-2,3,3-$d_3$ acid, 1 μg/mL itaconic acid-13C5, 0.1 μg/mL methylmalonic acid-$d_3$, or 0.1 μg/mL 2-methylcitric acid-$d_3$.

All samples were extracted with 80% methanol for 10 minutes at room temperature, followed by centrifugation for 10 min at 15,000 rpm, and the supernatants were sent to the Washington University Metabolomics Facility for LC-MS/MS analysis. Bacterial pellets from in vitro growth were resuspended in 500 μL of 80% methanol. For samples obtained from infected macrophages, $1\times10^6$ cells were infected, and at defined time points they were washed twice in PBS and extracted with 500 μL of 80% methanol. Sputum samples were liquefied before methanol extraction by adding Sputolysin (Calbiochem) in a 1:1 proportion. For the plasma and sputum samples, samples were added to 100% methanol to achieve a volume of 500 μL of extraction buffer at a final concentration of 80% methanol. The measurement of 4-cholesten-3-one, methylsuccinic acid, itaconic acid was performed with a Shimadzu 20AD HPLC system (Shimadzu, Columbia, MD) coupled to a Q Exactive mass spectrometer or 4000QTRAP mass spectrometer (AB Sciex, Framingham, MA). The 4-cholesten-3-one was separated on an ACE C8 (4.6×100 mm, 3μ) column (Mac-Mod Analytical, Chadds Ford, PA) and detected with positive multiple reaction monitoring (MRM) mode. The methylsuccinic acid and itaconic acid were separated on a ZIC-HILIC (4.6×150 mm, 3μ) column and detected with negative MRM mode. Quality control samples were prepared by pooling a portion of the study samples and were injected after every 10 study samples to monitor instrument performance. Data processing was conducted with Analyst 1.6.3. Metabolite abundance is reported for unprocessed samples (plasma or non-liquefied sputum).

Bacterial infections: For in vitro macrophage assays, a log-phase culture of Mtb was pelleted and resuspended in macrophage culture medium. Bacterial single-cell suspensions were prepared by low speed centrifugation (800 rpm for 8 minutes). The number of Mtb in the resulting supernatant was estimated by measuring absorbance at 600 nm, followed by infection of macrophages at a multiplicity of infection (MOI) of 1, 5, or 10. The infectious dose administered was calculated by plating CFU from an aliquot of the bacterial suspension. After 4 h, macrophages were washed three times with warm media to remove extracellular bacteria. To estimate intracellular Mtb growth, infected macrophages were lysed in 0.06% sodium dodecylsulfate (SDS) solution at the indicated time points, and serial dilutions of the lysates were plated on 7H10 agar plates (catalog no. 283810; BD Biosciences) containing glycerol and Middlebrook OADC enrichment (oleic acid-albumin-dextrose-catalase, catalog no. 212351; BD Biosciences). The number of CFU were calculated 14 to 21 days later.

Clinical study design: The goal of the study was to determine whether cholestenone, cholesterol, methylsuccinate, or itaconate levels were different in TB positive subjects compared to TB negative controls. Paired sputum and plasma samples were obtained from 20 TB positive and 20 TB negative subjects from Peru and Vietnam from the Foundation for Innovative New Diagnostics (FIND). The TB negative samples were from subjects who tested negative on sputum smear, culture, Xpert, and Quantiferon testing. These subjects had symptoms consistent with TB, but their symptoms improved or resolved at follow-up without treatment. The TB positive samples were from sputum smear, culture, and Xpert positive subjects who had symptoms consistent with Mtb infection. All patients were adults (≥18 years) and confirmed HIV negative. The study was exploratory, and no power analysis was performed. 160 samples from 80 subjects were requested from two different geographic areas. The investigators who processed the samples and quantified the metabolites were blinded to sample identity. No outliers were excluded. Total cholesterol was estimated in the plasma and liquefied sputum samples using the Amplex Red Cholesterol Assay kit.

Results

Figure 1B:
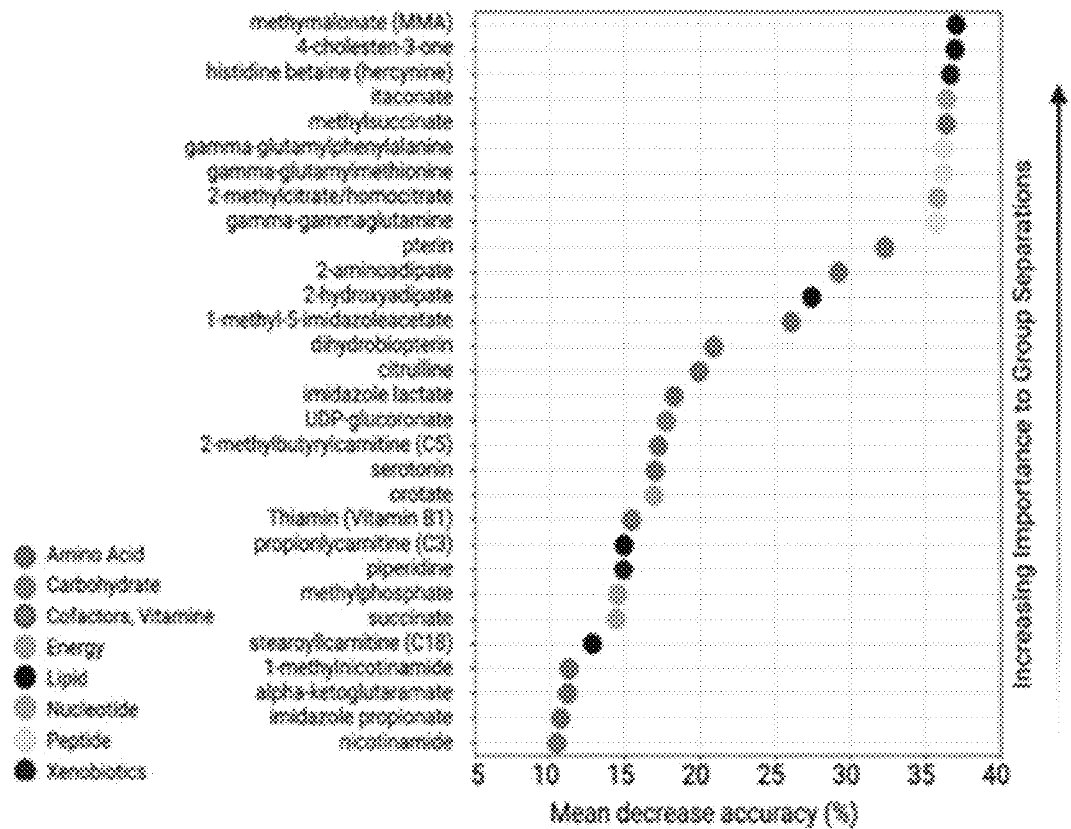
Figure 2:
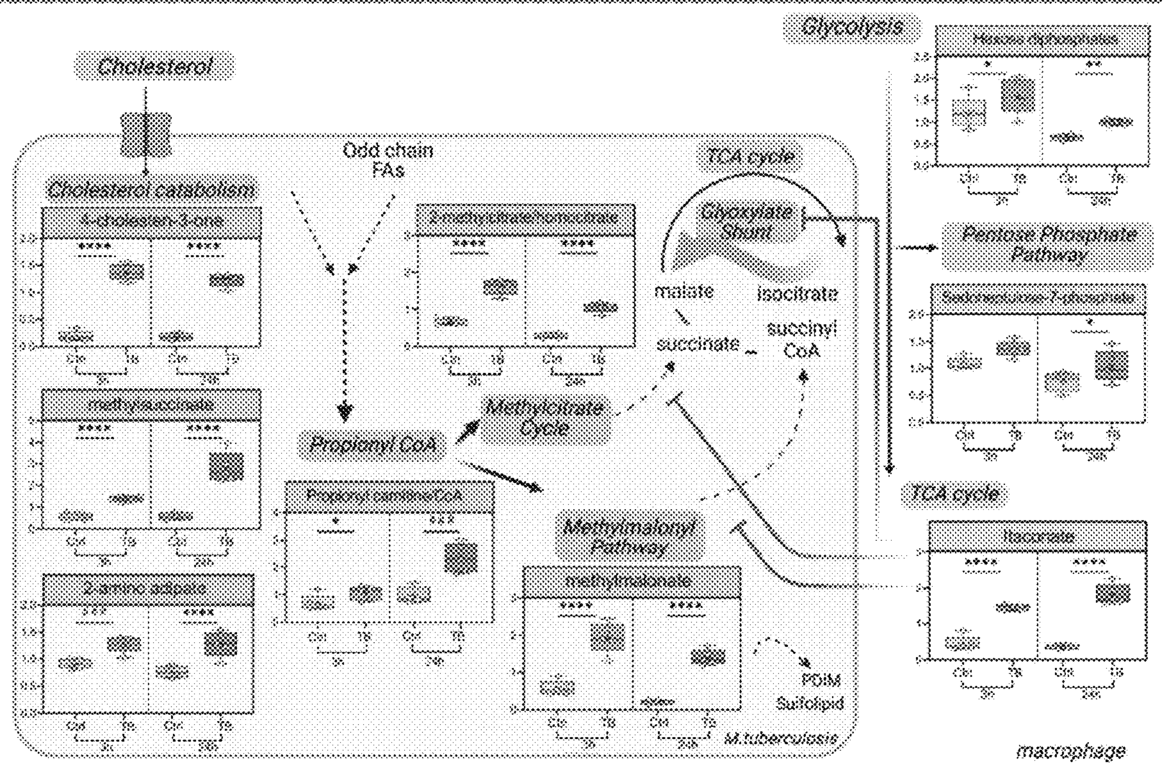
FIG. 2 is a schematic showing the metabolic signature of Mtb infection reflects changes in cholesterol metabolism. Schematic summarizing the relationship between key metabolic pathways and biochemicals that changed in response to infection. Metabolites that are likely from macrophages are orange, and those from Mtb are purple. Box plots show scaled intensity for relevant metabolites from the metabolomics screen in uninfected (Ctrl) and Mtb-infected (TB) samples 3 and 24 hpi. Box plots show median as a line and mean as '+', and each dot represents data from a single replicate. Statistical significance was calculated using ANOVA for all analytes identified in the screen. *$p<0.05$, $p<0.01$, ###$p\leq0.003$, and **$p<0.0001$.

Global metabolomics reveal immuno-metabolic changes and a signature of cholesterol metabolism associated with Mtb infection: To identify a metabolic signature of Mtb-infection, globally profiled metabolites from Mtb-infected bone marrow-derived macrophages (BMDM) at 7 and 28 hours post-infection (hpi) were compared to uninfected cells (FIG. 1A). Over 500 metabolites were reported from pathways involved in carbohydrate, lipid, nucleotide, and amino acid metabolism, redox homeostasis, inflammation, and xenobiotics. Since metabolite extraction was performed without separating intracellular Mtb from the macrophages, the identified metabolites could be from host or pathogen. Principle component analysis demonstrated clear separation of infected and uninfected samples, indicative of distinct metabolic phenotypes. Using Random Forest analysis, we identified 30 metabolites that distinguished Mtb-infected from uninfected macrophages and ranked them according to their predictive power (FIG. 1B). While differences in any individual metabolite from this global screen would require further validation, the overall changes were consistent with the idea that Mtb infection induces a Warburg-like glycolytic shift in macrophage metabolism, enhances flux to the pentose phosphate pathway for NADPH production, elevates itaconate levels, and alters redox homeostasis (gamma-glutamyl amino acids and pterin derivatives) (FIG. 1B and FIG. 2). Compared to controls, Mtb-infected macrophages showed elevated itaconate, the fourth most discriminating metabolite (FIG. 1B, FIG. 2). Classically activated macrophages have a characteristic TCA cycle breakpoint, which allows conversion of cis-aconitate to the antimicrobial metabolite itaconate by the enzyme Irg1. Irg1 protects against severe pathology in Mtb-infected mice. Mtb infection also enhanced levels of nucleotide sugars (UDP-glucuronate), which may be used by the host for glycosylation reactions or by Mtb to support cell wall biosynthesis. Overall, infection-induced molecules suggested upregulation of pathways that are metabolic hallmarks of an inflammatory macrophage phenotype.

Figure 3A:
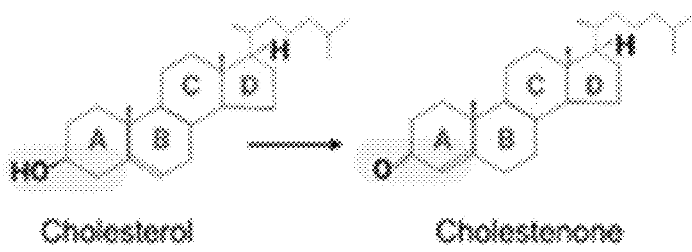
FIG. 3A, FIG. 3B, FIG. 3C, FIG. 3D, FIG. 3E, FIG. 3F, FIG. 3G, and FIG. 3H show macrophage cholestenone levels correlate with Mtb burden and duration of infection.

The other notable signature that was observed related to cholesterol utilization. The second most infection-discriminating metabolite was cholestenone, an oxidized-derivative of cholesterol (FIG. 2, FIG. 3A). Many of the other top metabolites, including methylsuccinate, methylcitrate, and 2-aminoadipate, were all previously enriched when Mtb was grown in vitro with cholesterol as compared to glycerol (FIG. 2). The top fifth discriminating metabolite was methylsuccinate, which may be generated by cholesterol C and D ring degradation (FIG. 1B, FIG. 2). It can also be produced through catabolism of branched chain amino acids, but since no major changes in valine and isoleucine catabolites were observed, the most likely source of methylsuccinate was degradation of host cholesterol by intracellular Mtb. Degradation of cholesterol and odd chain fatty acids by Mtb generates propionyl-CoA, which is in equilibrium with propionylcarnitine, another infection-induced metabolite identified in our screen (FIG. 2). Propionyl-CoA feeds the methylmalonate pathway and methylcitrate cycle, which generate important products for synthesis of bacterial virulence lipids and central carbon metabolism (FIG. 2). In response to infection, significant increases of methylmalonate and 2-methylcitrate, two intermediates of these metabolic pathways were detected. Interestingly, itaconate inhibits host and Mtb methylmalonyl-CoA mutase, which isomerizes methylmalonyl-CoA to succinyl-CoA. Itaconate also inhibits Mtb isocitrate lyase(s), which functions in the methylcitrate cycle. Thus, elevated itaconate may contribute to the observed elevation in methylmalonate and methylcitrate. Overall, our metabolomics screen suggested dynamic immuno-metabolic changes attributable to host-pathogen interactions. The results also pointed to the oxidation and degradation of cholesterol by the bacilli. This is consistent with a previous study in Mtb-infected THP-1 macrophages in which the cholesterol metabolite 4,5-9,10-diseco-3-hydroxy-5,9,17-tri-oxoandrosta-1 (10),2-diene-4-oic acid (DSHA) was detected. In the present example, the screening platform did not look for secosteroid and androstenedione-related metabolites that are intermediates in Mtb cholesterol degradation, such as DSHA, 4-androstenedione (ADD), 9-hydroxy-androsta-1,4-diene-3,17-dione (9OHADD), and 3-hydroxy-9,10-seconandrost-1,3,5(10)-triene-9,17-dione (3-HSA). Despite this limitation, among a vast pool of host metabolites, the apparent signature of cholesterol metabolism was noteworthy. Since cholestenone is a unique metabolite that is likely to depend upon host and Mtb co-metabolism, its production during intracellular infection was further investigated.

Figure 3B:
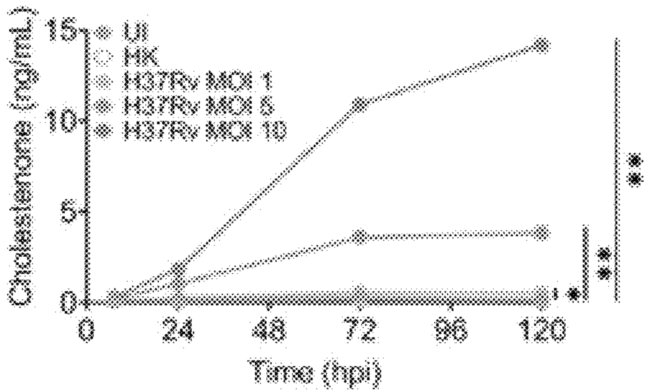
Figure 3C:
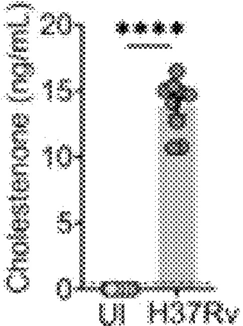
Figure 3D:
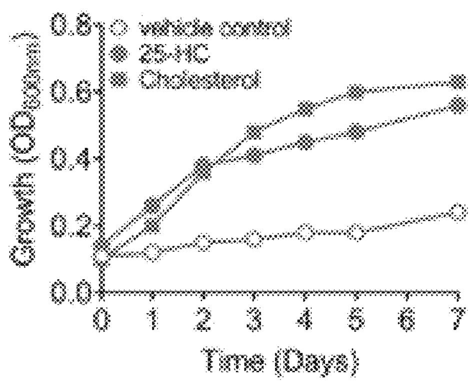
Figure 3E:
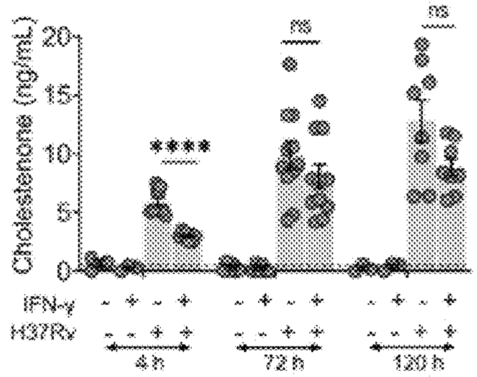
Figure 3F:
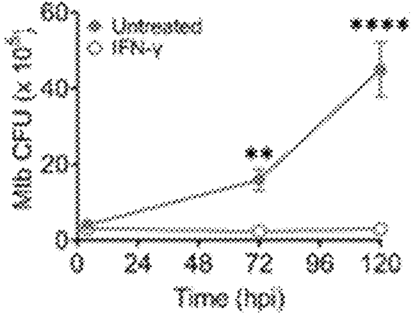

Cholestenone abundance correlates with bacterial burden and duration of Mtb infection: BMDMs were infected with Mtb at different multiplicities of infection (MOI) and estimated cholestenone abundance at various time points over five days of infection using mass spectrometry. During metabolite extraction, cell lysates were spiked with pre-measured d5-cholestenone as an internal standard to verify the identity of the metabolite and to quantify its relative abundance. Cholestenone levels were found increased with increasing bacterial burden and duration of infection (FIG. 3B). As a control, heat-killed Mtb was used, which confirmed that cholestenone production requires live bacilli. It was also verified that Mtb infection generated cholestenone in human cells by infecting THP-1 macrophages, a human monocytic cell line (FIG. 3F). In addition, the levels of methylmalonate, methylcitrate and methylsuccinate were examined, additional top differential metabolites related to cholesterol degradation, and itaconate. the corresponding internal standards were included for each metabolite during extraction. It was confirmed that Mtb infection enhanced the level of methylsuccinate and itaconate 72 hpi (FIG. 7B). differences in the abundance of methylcitrate and methylmalonate 72 hpi were not detected so their apparent elevation at earlier time points in the primary screen requires further validation. Thus, a sustained increase in abundance of methylsuccinate, cholestenone, and itaconate was confirmed in response to Mtb infection of BMDMs.

Figure 3G:
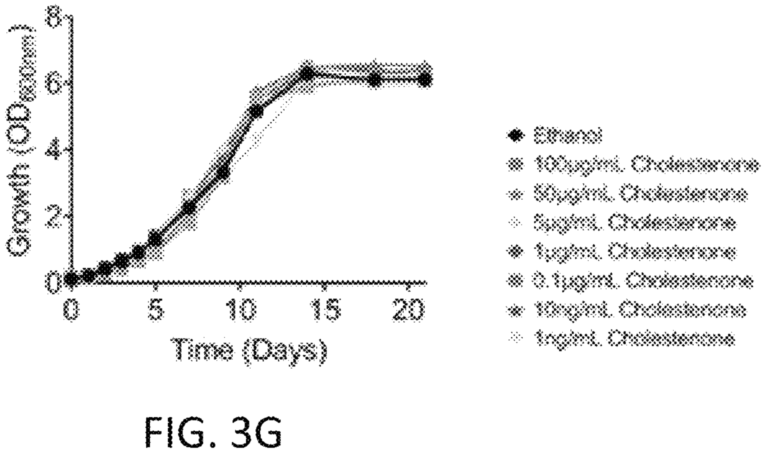
Figure 3H:
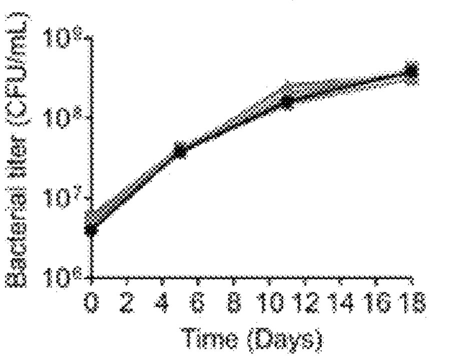

Recent reports show that IFN-γ induces the expression of cholesterol 25-hydroxylase, which converts cholesterol to the immunomodulatory oxysterol 25-hydroxycholesterol (25-HC) which can have antimicrobial activity. Since IFN-γ activation also enhances the ability of macrophages to control Mtb, the ability of Mtb to metabolize 25-HC was investigated. First, whether Mtb can use 25-HC as a carbon source was examined and found that Mtb grew in minimal media supplemented with 25-HC as the sole carbon source (FIG. 3D). Next, IFN-γ-activated and untreated BMDMs were infected and compared cholestenone abundance at various time points of infection (FIG. 3E). At the same time, a standard curve to determine the linear range of the assay was generated to establish the concentration of cholestenone in samples. In addition, total cholesterol, Mtb burden, and macrophage cell viability at each time point was quantified (FIG. 3F). Mtb infected both naïve and IFN-γ-activated macrophages equally, however, macrophages that had been pre-treated with IFN-γ had significantly reduced cholestenone abundance early (4 hours) after infection. At 72 and 120 hpi, cholestenone levels trended lower but were not significantly different between treated and untreated macrophages (FIGS. 3E and 3F) even though bacterial colony forming units (CFU) were significantly lower in the IFN-γ-treated macrophages. Thus, IFN-γ treatment appears to influence the relationship between bacterial burden and cholestenone levels. Although total cholesterol levels were not impacted by IFN-γ, IFN-γ profoundly impacts the intracellular niche of the Mtb and as well as host metabolism, including altering the distribution of different host cholesterol pools. Thus, IFN-γ might alter cholestenone production or subsequent metabolism by impacting host or bacterial metabolism. To determine whether cholestenone could have direct antimicrobial activity against Mtb, its impact on bacilli growing in broth culture was evaluated. It was found that cholestenone was not directly toxic to Mtb, even at concentrations in vast excess of what was found in macrophages (FIGS. 3G and 3H). Taken together, these findings demonstrate that Mtb infection of IFN-γ-activated and naïve macrophages leads to the production of cholestenone, an oxidized-derivative of host cholesterol.

Figure 4A:
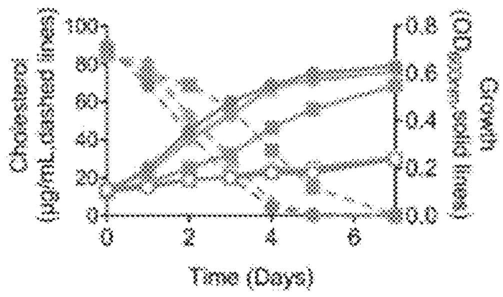
FIG. 4A, FIG. 4B, FIG. 4C, FIG. 4D, FIG. 4E, FIG. 4F, and FIG. 4G show Mtb 3p-hydroxysteroid dehydrogenase, not ChoD, catalyzes oxidation of cholesterol to cholestenone.
Figure 4B:
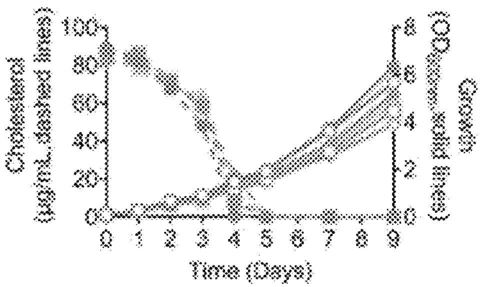
Figure 4C:
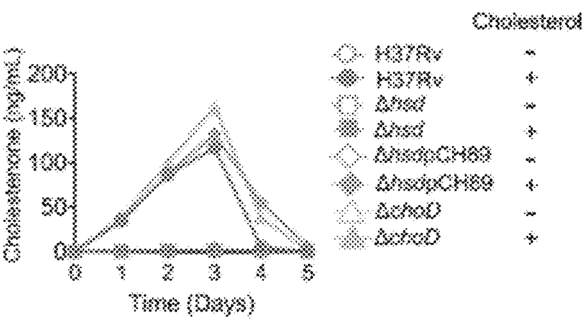
Figure 4D:
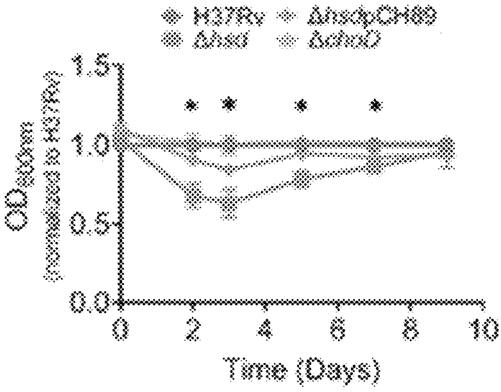
Figure 4E:
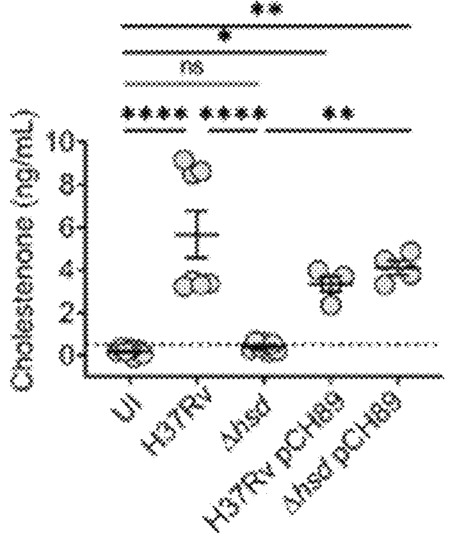
Figure 4F:
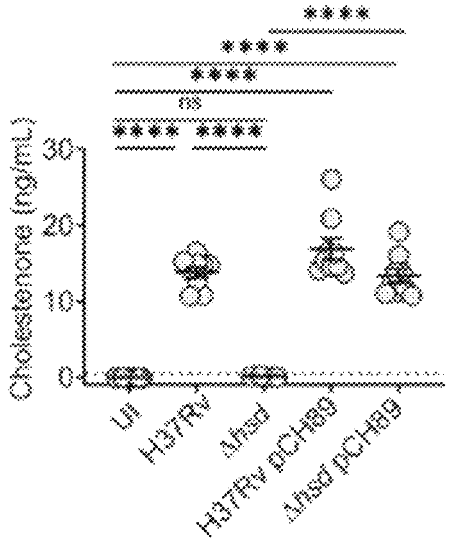
Figure 4G:
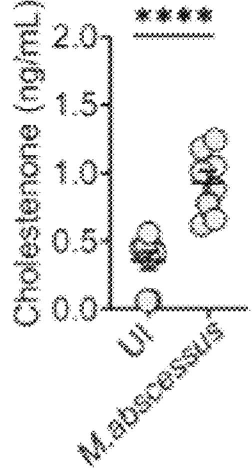

3β-hydroxysteroid dehydrogenase, not ChoD, converts cholesterol to cholestenone: As far as we are aware, there is no mammalian enzyme that is reported to convert cholesterol to cholestenone. There is ambiguity in the literature as to the identity of the enzyme that is responsible for cholestenone production by Mtb and whether the oxidation step is required for cholesterol degradation. The enzymes that have been evaluated in previous studies are 3β-hydroxysteroid dehydrogenase (3β-Hsd, Rv1106c) and cholesterol oxidase (ChoD, Rv3409). Purified 3β-Hsd has cholesterol oxidase activity in vitro. However, in the H37Rv strain background, a Δhsd mutant metabolizes cholesterol to degradative intermediates and grow on cholesterol. ChoD (Rv3409) has been investigated as an alternative cholesterol oxidase, but the H37Rv Δhsd ΔchoD double mutant is also reported to grow on cholesterol. Given the apparent contradictory results, the cholesterol oxidase(s) in our strain and determine whether it was required for cholesterol degradation was investigated. Oligonucleotide-mediated Recombineering was used followed by Bxb1 Integrase Targeting (ORBIT) to delete hsd (Δhsd) or choD (ΔchoD) in the H37Rv strain background. these strains were grown in liquid cultures using either minimal or a nutrient-rich media (7H9 with oleic acid, albumin, dextrose, catalase, and glycerol), supplemented with either vehicle control or 0.1 mg/mL cholesterol solubilized in tyloxapol:ethanol (FIGS. 4A and 4B). Growth of wild type (WT) and mutant strains were monitored and quantified cholesterol and cholestenone abundance. As expected, the mutants and parental strain grew similarly in nutrient rich media, irrespective of whether it was supplemented with cholesterol or not (FIG. 4B). In these conditions, cholesterol levels decreased over time and became undetectable by Day 5. In minimal media, all the strains grew when cholesterol was provided as the sole carbon source (FIG. 4A). The ΔchoD strain was indistinguishable from WT, whereas the Δhsd mutant had a slight growth delay during the exponential growth phase, accompanied by a slight delay in depleting cholesterol in the media (FIG. 4A). However, despite the modest impact on cholesterol utilization, a drastic decrease in cholestenone production as observed in the Δhsd mutant compared to the WT strain and ΔchoD mutant, which was restored by complementation (FIG. 4C). Thus, neither ChoD nor 3β-Hsd are required for growth of Mtb on cholesterol at the sole carbon source, although 3β-Hsd was required for cholestenone production. The modest growth delay of Δhsd was reproducible and restored by complementation (FIG. 4D). Together, these results indicate that 3β-Hsd is required for cholestenone production by Mtb in vitro. Importantly, since the Δhsd mutant is capable of growing on cholesterol even though it cannot produce cholestenone (FIGS. 4A and 4C), these results show that cholestenone production is not absolutely essential for cholesterol utilization in Mtb. To determine whether 3β-Hsd was essential for cholestenone production during intracellular infection, cholestenone abundance in BMDMs infected with Mtb and the Δhsd mutant were compared. Cholestenone was not detected in macrophages infected with the Δhsd mutant, and genetic complementation restored the production of cholestenone (FIG. 4E). In BMDMs that were pre-treated with IFN-γ, cholestenone made during Mtb infection was also dependent on the bacterial 3β-Hsd. The same was found in PMA-differentiated THP-1 macrophages (FIG. 4F). The dependence of cholestenone on bacterial 3β-Hsd was not due to attenuation of the mutant strain, as intracellular uptake and growth of Δhsd was similar to WT Mtb. Lastly, to determine whether non-tuberculous *mycobacterium* (NTM) also generated cholestenone during infection, BMDMs were infected with *Mycobacterium abscessus*, an important cause of pulmonary disease, particularly in patients with cystic fibrosis. As for Mtb, it was found that in macrophages infected with *M. abscessus*, host cholesterol was oxidized to cholestenone (FIG. 4G). To conclude, 3β-Hsd was confirmed to be required for the oxidation of cholesterol into cholestenone by Mtb; however, 3β-Hsd is not required for cholesterol utilization by Mtb. In addition, cholestenone is also produced during macrophage infection with *M. abscessus*, consistent with the presence of cholesterol oxidases in mycobacterial species beyond Mtb.

Figure 5A:
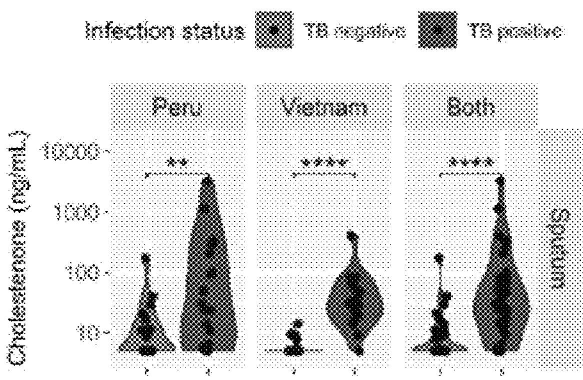
FIG. 5A, FIG. 5B, FIG. 5C, FIG. 5D, FIG. 5E, FIG. 5F, FIG. 5G and FIG. 5H show cholestenone levels are elevated in clinical samples from TB patients. Levels of metabolites from clinical samples from TB negative (n=20 per country) and TB positive subjects (n=20 per country)
Figure 5B:
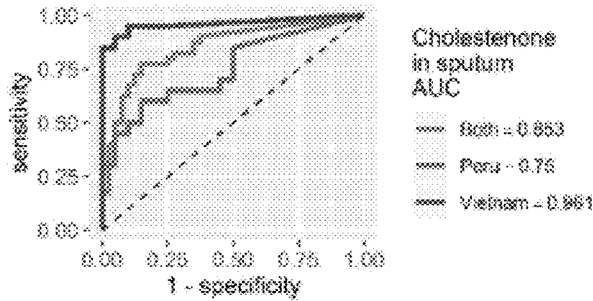
Figure 5C:
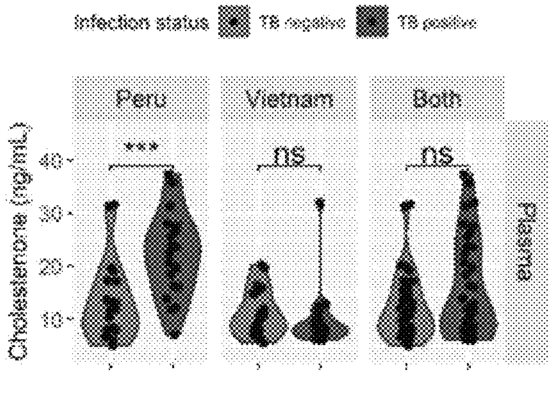
Figure 5D:
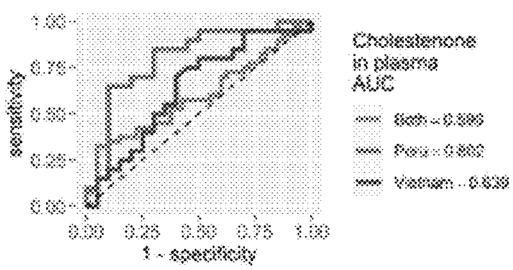
Figure 5E:
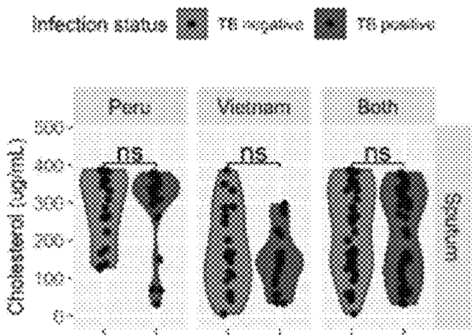
Figure 5F:
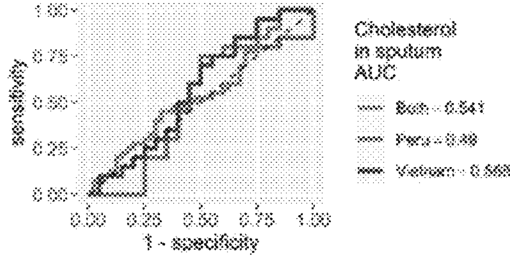
Figure 5G:
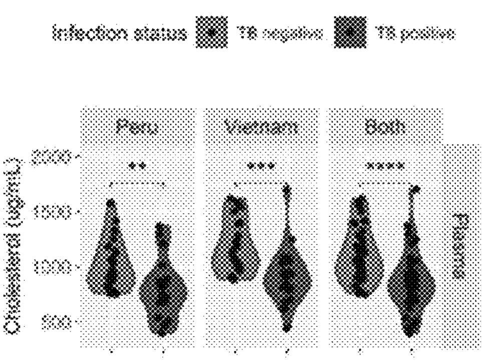

Cholestenone levels are elevated in clinical samples from TB patients: Based upon the in vitro results, it was investigated whether methylsuccinate, cholestenone, and itaconate are more abundant in TB patients compared to controls. Paired sputum and plasma samples were obtained from 80 patients from Peru and Vietnam. All patients were ≥18 years old and HIV negative. The TB-positive group (n=20 per country) were positive by sputum smear microscopy and culture. Importantly, subjects in the control group (n=20 per country) had symptoms compatible with TB infection, but they were negative for active TB by sputum smear microscopy, culture, and Xpert, as well as having negative QuantiFERON assay results. There were no significant differences in the age range or sex of TB-positive or negative subjects in either country (Table 1). Their clinical symptoms, such as chest pain, recent weight loss, fever, dyspnea and hemoptysis were recorded (Table 1). Metabolites were extracted from sputum and plasma samples and measured methylsuccinate, cholestenone, and itaconate levels by mass spectrometry. Since itaconate is produced as a general host response to infection, it was thought it might be present in both TB-infected and uninfected subjects, since the TB-negative subjects might have other infections. However, in most subjects, itaconate was undetectable, and we found no significant differences in levels of itaconate or methylsuccinate in sputum or plasma of TB-positive subjects compared to controls. It was anticipated that cholestenone would be TB-specific, since no evidence could be found that it was made by common pulmonary pathogens. Indeed, the sputum of TB-positive subjects had significantly higher cholestenone abundance compared to controls, in both the Peru and Vietnam cohorts (FIG. 5A, Mann-Whitney $p<0.01$ and $p<0.0001$ respectively). To assess the precision of the mass spectrometry quantification, the sputum processing and mass spectrometry analysis were repeated for 80 samples and found a high degree of correlation between the independent experiments. Receiver operating characteristic (ROG) analysis showed that the levels of cholestenone in sputum had high TB diagnostic potential in Vietnam (AUC=0.96), and Peru (AUC=0.75) (FIG. 5B). In addition to higher levels of cholestenone in sputum, TB patients in the Peru cohort also had significantly higher plasma cholestenone compared to controls (FIG. 5C, t-test $p<0.001$). Remarkably, plasma levels of cholestenone were predictive of TB infection in subjects from Peru (FIG. 5D, AUC=0.80). However, plasma cholestenone levels were not significantly associated with TB-infection status in the Vietnam cohort and showed poor predictive value (FIGS. 5C and 5D, AUC=0.64). While sputum cholestenone levels were elevated in subjects with TB, sputum cholesterol levels were not different between TB-infected and control subjects and were therefore of little predictive value (FIGS. 5E and 5F). Plasma cholesterol levels in both cohorts were significant lower in TB subjects compared to controls (FIG. 5G, t-test $p<0.01$ and $p<0.001$ for Peru and Vietnam cohorts, respectively).

TABLE 1

Summary statistics for clinical variables by country and infection status.

| Variable | Peru TB negative (N = 20) | Peru TB positive (N = 20) | P-value* | Vietnam TB negative (N = 20) | Vietnam TB positive (N = 20) | P-value* |
|---|---|---|---|---|---|---|
| Sex Female | 9/20 (45%) | 6/20 (30%) | 0.327 | 7/20 (35%) | 5/20 (25%) | 0.49 |
| Male | 11/20 (55%) | 14/20 (70%) | | 13/20 (65%) | 15/20 (75%) | |
| Age; mean (SD) | 33 (11.6) | 30 (10.9) | 0.471 | 51 (15.6) | 47 (14.1) | 0.412 |
| History of BCG vaccination | 18/19 (90%) | 20/20 (100%) | 0.487 | 9/17 (45%) | 13/15 (65%) | 0.06 |
| History of active TB | 0/8 (0%) | 1/20 (5%) | >0.999 | 5/20 (25%) | 3/20 (15%) | 0.695 |
| Normal chest x-ray | 14/17 (82%) | 1/19 (5%) | <.001 | 0/20 (0%) | 0/20 (0%) | >0.999 |
| Chest pain | 18/20 (90%) | 13/20 (65%) | 0.058 | 9/20 (45%) | 11/20 (55%) | 0.527 |
| Dyspnea | 11/20 (55%) | 14/20 (70%) | 0.327 | 14/20 (70%) | 8/20 (40%) | 0.057 |
| Fever | 6/20 (30%) | 11/20 (55%) | 0.110 | 12/20 (60%) | 13/20 (65%) | 0.744 |
| Hemoptysis | 3/20 (15%) | 8/20 (40%) | 0.155 | 4/20 (20%) | 5/15 (25%) | >0.999 |
| Malaise | 20/20 (100%) | 19/20 (95%) | >0.999 | 16/20 (80%) | 14/20 (70%) | 0.716 |
| Night sweats | 4/20 (20%) | 12/20 (60%) | 0.022 | 6/20 (30%) | 9/20 (45%) | 0.327 |
| Cough | 20/20 (100%) | 20/20 (100%) | >0.999 | 20/20 (100%) | 20/20 (100%) | >0.999 |
| Recent weight loss (without diet) | 7/20 (35%) | 15/20 (75%) | 0.011 | 6/20 (30%) | 11/20 (55%) | 0.11 |

Results reported as n (%) or mean (range).

*P-values obtained using a chi-square, fishers exact, or t-test, as appropriate.

Figure 5H:
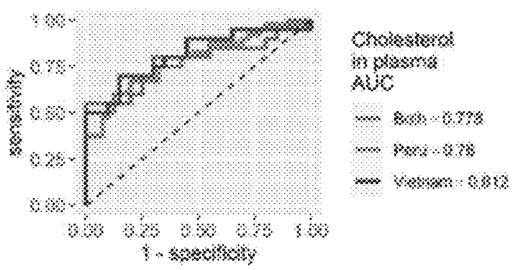
Figure 6A:
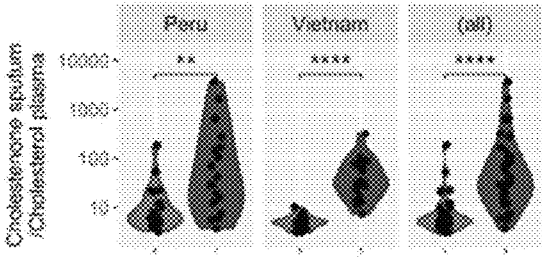
FIG. 6A, FIG. 6B, FIG. 6C and FIG. 6D shows Ratio of cholestenone to plasma cholesterol in clinical samples from TB patients improves the diagnostic accuracy. Ratios of metabolites from clinical samples from TB negative (n=20 per country) and TB positive subjects (n=20 per country) FIG. 6A Ratio of sputum cholestenone and plasma cholesterol of control and TB-positive subjects from both countries and the FIG. 6B corresponding ROC curve.
Figure 6B:
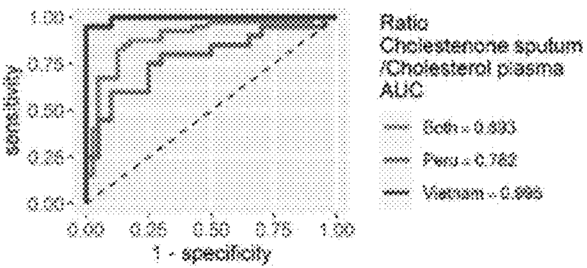
Figure 6C:
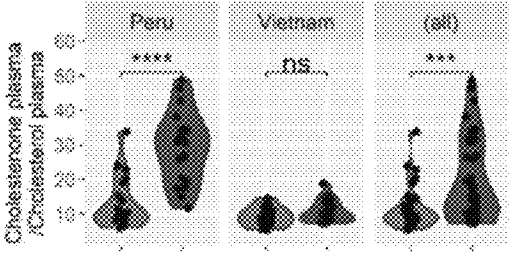
Figure 6D:
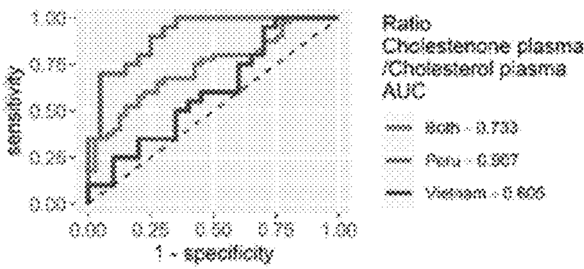

Consistent with these observations, ROG plots for cholesterol abundance in plasma show a similar performance for both cohorts (FIG. 5H, AUC=0.81 in Vietnam and AUC=0.78 in Peru). Furthermore, a ratio of sputum cholestenone and plasma cholesterol was significantly increased in TB-positive subjects compared to controls in both countries, and using the ratio improved the discriminating potential of these metabolites (FIGS. 6A and 61B, AUC=0.995 in Vietnam, AUC=0.78 in Peru cohorts). Consistent with the observations for cholestenone plasma levels in TB positive subjects from Peru, the ratio of plasma cholestenone and plasma cholesterol was significantly higher in Peru TB subjects than controls and had a high diagnostic accuracy (FIGS. 6C and 6D, AUC=0.90 in Peru). To conclude, the present example shows that bacterial-derived cholestenone, which is a dominant metabolic signature of Mtb infection in macrophages, is elevated in samples from TB-infected subjects in a clinical setting.

Figure 7A:
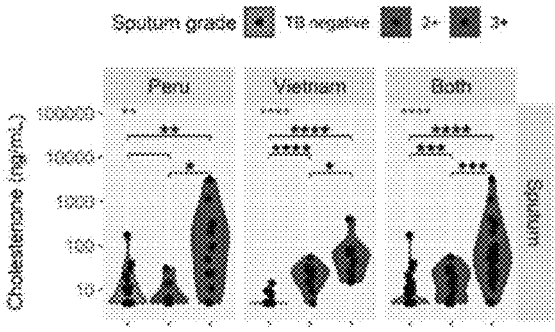
FIG. 7A, FIG. 7B, FIG. 7C, FIG. 7D, FIG. 7E and FIG. 7F show cholestenone abundance in sputum of TB patients correlates with infection burden. Levels of metabolites are plotted for TB negative subjects and TB positive subjects grouped according to sputum grade, for FIG. 7A cholestenone in sputum, FIG. 7B cholestenone in plasma, FIG. 7C cholesterol in sputum, FIG. 7D cholesterol in plasma, FIG. 7E the ratio of cholestenone in sputum divided by cholesterol in plasma, FIG. 7F the ratio of cholestenone in plasma divided by cholesterol in plasma. Results are shown for each country (n=40) as well as both countries pooled (n=80). The ratios were determined on a per-subject basis and are shown multiplied by a factor $10^6$ for clarity Statistical analyses were done using the Kruskal-Wallis test (blue asterisks) followed by pairwise comparisons with the Mann-Whitney test with the Benjamini-Hochberg correction for multiple comparisons. The resulting adjusted p-values are shown with black asterisks. For all statistical tests, significance is indicated with the following: *p<0.05, p<0.01, *p<0.001, ****p<0.0001. Lack of asterisks indicates p>0.05.
Figure 7B:
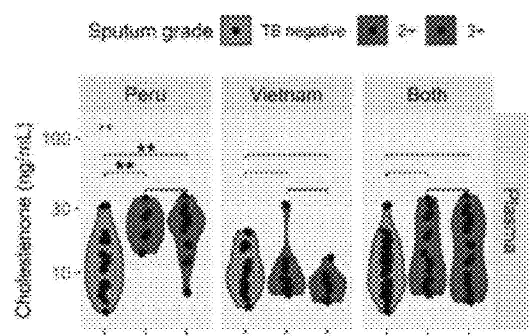
Figure 7C:
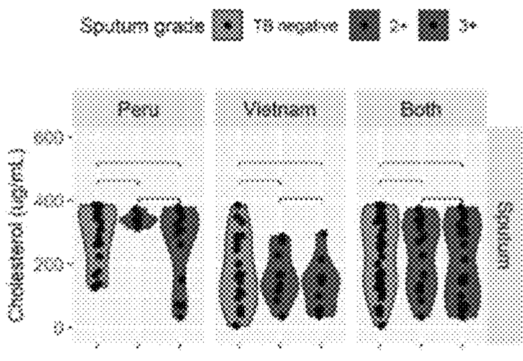
Figure 7D:
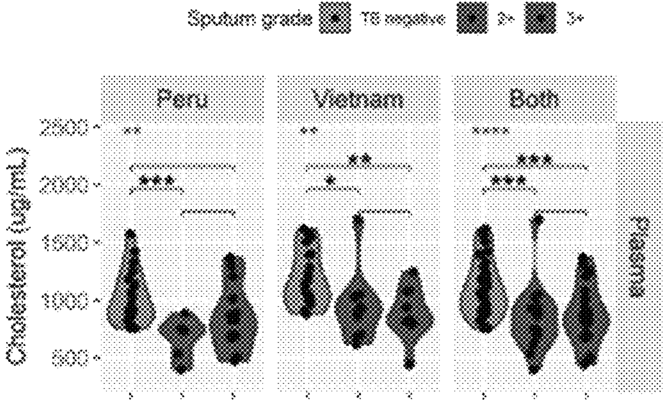
Figure 7E:
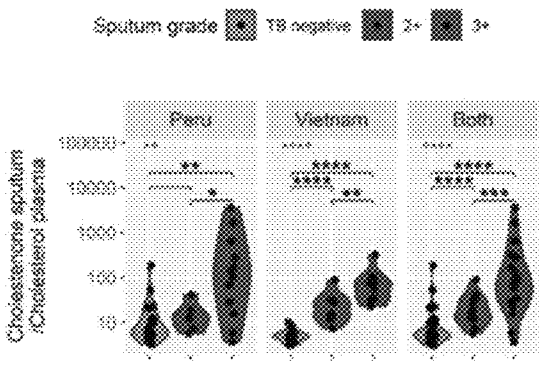
Figure 7F:
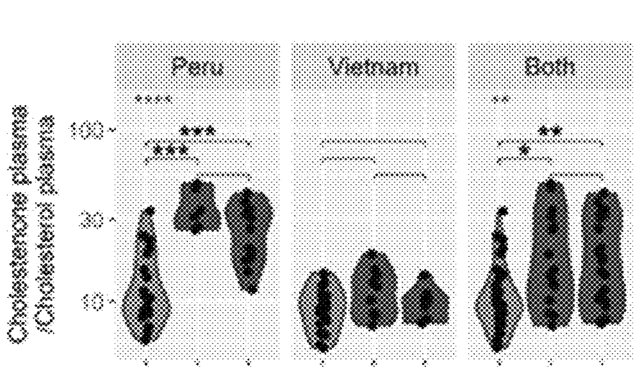

Cholestenone abundance in sputum of TB patients correlates with infection burden: Next, it was assessed whether clinical characteristics of the TB-positive subjects influenced cholestenone and cholesterol levels in sputum or plasma. First, TB positive patients were grouped from both Peru and Vietnam (n=40) according to sputum grade (2+ or 3+) and compared each group with TB negative subjects (n=40) (FIG. 7). It was found that the cholestenone levels in sputum were higher for the 2+ subjects compared to TB negative subjects (FIG. 7A, adjusted p-value <0.001), and a further increase was seen in sputum of the 3+ subjects compared to 2+ subjects (FIG. 7A, adjusted p-value <0.001), suggesting that sputum cholestenone abundance correlates with Mtb burden in the lungs. In contrast, there was no difference in plasma cholestenone levels based upon sputum grade (FIG. 7B). Cholesterol levels in sputum were also not different between subjects based on sputum grade (FIG. 7C). Plasma cholesterol levels were decreased in 2+ positive and 3+ positive subjects compared to TB negative subjects, however there was no difference between 2+ and 3+ subjects (FIG. 7D). Next, the TB-positive subjects were grouped from both countries (n=40) and investigated whether metabolite levels were associated with other clinical parameters such the subject's sex or presence of specific clinical symptoms. We found no clinical parameter that was significantly associated with cholestenone or cholesterol levels in the sputum of TB-positive subjects. Plasma cholesterol, however, was significantly lower in patients with hemoptysis, a sign of advanced disease (t-test $p<0.05$). To conclude, the present example shows that sputum cholestenone level in TB patients correlates with the degree of smear positivity, suggesting it reflects pulmonary pathogen burden.

Discussion

In this example, the metabolic landscape of Mtb-infected macrophages was investigated. It was found that the host recalibrates its metabolism to support immune effector functions. Mtb infection induces a Warburg-like glycolytic shift, enhances flux to the pentose phosphate pathway, and modifies the TCA cycle for generating the antimycobacterial metabolite itaconate, the top fourth differential biochemical in our screen. This intracellular milieu poses a challenge for most microbes, but Mtb is highly adapted to survive this environment. It was found that the most prominent metabolic signature of Mtb infection is likely to reflect bacterial cholesterol degradation. Bacterial cholesterol metabolism results in propionyl-CoA, which is metabolized through the methyl citrate and methylmalonyl pathway, and propionyl-CoA, 2-methylcitrate, and methylmalonate were infection-induced metabolites. In addition, previous work has shown that growing Mtb in the presence of cholesterol results in elevated levels of methylsuccinate and 2-aminoadipate, also top differential metabolites in this study. The abundance of other metabolites of cholesterol degradation by Mtb, such as ADD, 9OHADD, DSHA, or 3-HSA cannot be inferred because they were not included in the panel of queried metabolites in the screening platform. Since humans do not degrade cholesterol through a similar pathway, this raised the possibility that unique cholesterol metabolites, such as cholestenone, might be biomarkers for infection. Indeed, it was found that the oxidized cholesterol metabolite, cholestenone, accumulates in Mtb-infected macrophages, and cholestenone levels in sputum correlate with active TB disease in two geographically distinct cohorts. While cholesterol utilization by Mtb has been linked to dormancy and persistence, the present data suggests that Mtb metabolizes cholesterol during active infection in people, consistent with expression profiling showing activation of the KstR regulon in Mtb isolated from sputum. The present data in macrophages suggest that intracellular Mtb has access to host cholesterol, and we anticipate that extracellular bacilli would also be able to metabolize cholesterol present extracellularly in caseum or sputum.

This data suggests that the vast majority of cholestenone present during Mtb infection is derived by host-pathogen co-metabolism, with the host providing cholesterol and the Mtb 3β-Hsd enzyme converting it to cholestenone. What is the evidence in support of this idea? First, recombinant Mtb 3β-Hsd has been shown to convert cholesterol to cholestenone in vitro. Mtb lacking Rv1106c, the gene encoding 3β-Hsd, fail to convert cholesterol to cholestenone when growing in liquid culture, as shown by others and verified by us (FIG. 4C). Applicants found that in macrophages the abundance of cholestenone that accumulates upon Mtb infection depends upon duration and multiplicity of infection (FIG. 3B). Importantly, cholestenone production in macrophages also depends upon the bacteria being alive and having the hsd gene (FIG. 3B, FIG. 4E, FIG. 4F). Thus, while it is theoretically possible that the cholestenone produced in macrophages is made by a host enzyme in response to wild type but not Δhsd mutant bacilli, the most straightforward explanation is that the cholestenone made during infection comes from 3β-Hsd of the bacilli. In addition, although humans have several 3β-HSD enzymes that bear 29-35% identity to the one in Mtb, as far as we are aware, no mammalian enzyme is reported to convert cholesterol to cholestenone. When the available published datasets were examined, mammalian 3β-hydroxysteroid dehydrogenases (HSD3B1 and HSD3B2) do not appear to be expressed in Mtb-infected murine macrophages, Mtb-infected human macrophages, and IFN-γ activated murine macrophages. This is not surprising since they are expressed in steroidogenic tissue where they dehydrogenate steroid hormones. Therefore, all the data combined suggest that Mtb 3β-Hsd converts cholesterol to cholestenone during macrophage infection.

Although the evidence strongly suggest that Mtb is the source of cholestenone during macrophage infections, how is it then that low levels of cholestenone in plasma of subjects without TB were detected? These subjects had plasma cholestenone levels in the range of 5-32 ng/ml, consistent with a previous report that demonstrated levels of 30.4+/−8.5 ng/ml from a pooled sample of plasma from 100 individuals representative of the US population. HSD3B1 and HSD3B2 catalyze the conversion of 3β-hydroxy steroids, which lack the side chain found on cholesterol, to the 3-keto configuration. They are expressed in the adrenals, ovaries, and testes, where they carry out an essential step in production of progesterone, androstenedione, and testosterone. HSD3B7 converts the 3β-hydroxy of 7α-hydroxycholesterol to the 3-keto configuration during bile acid synthesis. Cholestenone is not reported as an intermediate in either of these pathways. Thus, the source of the baseline cholestenone in the subjects without TB is not clear, but two recent publications suggest that it may be derived from cholesterol dehydrogenases expressed from uncultured members of the microbiome. Thus, while the present findings support the idea that in TB-infected subjects the elevated cholestenone is largely Mtb-derived, it could theoretically be microbiome-derived or the result of a yet-to-be-defined host enzyme.

Applicants found that although 3β-Hsd is required for cholestenone production, it is not required for cholesterol utilization, at least in the H37Rv strain background. This was somewhat surprising because cholesterol oxidation to cholestenone is often considered an initial event in cholesterol degradation. Cholesterol is degraded through β-oxidation of the cholesterol side chain and cleavage of the A and B rings, followed by degradation of the C and D rings. Side chain degradation is initiated by oxidation of the side chain at C26. In H37Rv, CYP125 and CYP142 can both perform this initiating step, and since both cholesterol and cholestenone are known substrates of CYP125 and CYP142, it is not surprising that this could occur without 3β-Hsd. However, the first enzyme involved in AB ring cleavage, KstD (Rv3537), strongly prefers androstendione (AD) as a substrate, which has a ketone at the third carbon, compared to a substrate with a β-hydroxy. It is possible that in the absence of 3β-Hsd, a different enzyme acts during or after cholesterol side chain degradation, for example, by converting the β-hydroxy of dehydroepiandrosterone to the 3-ketone of AD.

Previous studies showed that the Δhsd ΔchoD double mutant in the H37Rv strain background makes AD and 9-hydroxy androstendione (9OHAD), consistent with the idea that there is an enzyme other than 3β-Hsd and ChoD that can generate the ketone. It is also possible that there is metabolic flexibility and a ketone at C3 is not absolutely essential for Mtb to grow on cholesterol. To understand differences in how cholesterol and cholestenone are degraded in the absence of 3β-Hsd will require dedicated studies with labeled cholesterol and cholestenone. It should be pointed out that the present study is in agreement with two previous reports on the role of 3β-Hsd in cholesterol degradation and may resolve why they we are seemingly at odds with one another. As reported previously, we validated that Mtb 3β-Hsd is the major cholesterol-oxidizing enzyme that generates cholestenone, whereas ChoD appears to be dispensable for this activity (FIG. 4C). 3β-Hsd is not required for utilization of cholesterol. Thus, the apparent discrepancy between these previous studies is explained by the finding that the ability of Mtb to grow on cholesterol does not depend upon the oxidation of cholesterol to cholestenone. Previous studies have shown that cholestenone disrupts lipid rafts, membrane fluidity, and cell signaling in mammalian cells, and recent work shows that cholestenone has antimicrobial activity against *Helicobacter pylori*. During macrophage infections Applicants found that cholestenone appears to accumulate over time. Whether cholestenone remains associated with the bacilli or traffics to host membranes is an area for future investigation. Given that it is detected in both sputum and plasma in clinical samples, it seems likely that it is widely distributed and could have a biological impact. Since 3β-Hsd can also oxidize oxysterols, such as pregnenolone, Mtb might also modify steroid hormones. Interestingly, *Mycobacterium leprae* has lost the genes for cholesterol catabolism, but retains hsd and the ability to make cholestenone. In addition, in Mtb Rv1106c/hsd is not transcriptionally regulated with other genes required for cholesterol metabolism. Combined, these observations suggest that cholestenone or other 3β-Hsd-generated host-pathogen co-metabolites might be involved in pathogenesis. As described for tryptophan co-metabolism, the present work suggests that utilization of host cholesterol by Mtb has a role beyond bacterial nutrition.

Cholestenone does not appear to be a metabolite made by most pulmonary pathogens either. The literature suggests that cholestenone can be produced by a limited number of microbes that infect humans including Mycobacteria, *Rhodococcus* and *Nocardia*. In addition, a literature review on the top bacterial causes of pulmonary infections was performed and only identified reports of cholesterol oxidase activity by ChoD orthologs in *Acinetobacter, Pseudomonas*, and *Serratia*. However, there are several studies showing that putative cholesterol oxidases of *Pseudomonas* produce hydroperoxycholestenone (HCEO) rather than cholestenone. In addition, outside of Mycobacteria, there are very little data available on 3β-Hsd proteins in prokaryotes. Two recent publications report 3β-Hsd orthologs in bacterial species of the human gut microbiota. To our knowledge, no other reports describe 3β-Hsd family proteins in bacterial species outside of Mycobacteria. Thus, cholestenone is useful as a specific differential diagnosis biomarker of active TB disease, generated by the co-metabolism of host and pathogen. Indeed, it was found that cholestenone levels in sputum correlated with TB infection status in human patients. In the present study, the control group consisted of subjects presenting with symptoms consistent with TB, but in whom Mtb infection was ruled out. This suggests that the significantly elevated level of cholestenone in the TB positive group is specific to Mtb infection rather than a more general marker of lung infection or inflammation. Hypocholesterolemia was also observed in TB patient plasma in both Peru and Vietnam, a finding previously documented in populations in Turkey and Ethiopia. While there are many reasons this might be, it is tempting to speculate that consumption of cholesterol by Mtb contributes to reduced levels in the host. Taken together, a ratio of sputum cholestenone and plasma cholesterol showed excellent predictive accuracy for diagnosing TB in both Peru and Vietnam cohorts.

Interestingly, it was found that plasma cholestenone levels also correlated with TB infection status, but only in the Peruvian population. In sputum, the TB diagnostic potential of cholestenone was higher in Vietnam (AUC=0.96) than Peru (AUC=0.75). What might account for these differences? Cholestenone might be metabolized differently in the two populations because of differences in bacterial strains or host genetics. Since different lineages of Mtb predominate in Peru and Vietnam, there might be differences in how the bacilli metabolize cholesterol, which could contribute to differences in metabolites detected in people. Hsd is uniformly present in *M. tuberculosis* isolates, but it might be regulated differently, or other cholesterol metabolic genes may vary by lineage. Since different lineages have also been shown to have different predilection for extra-pulmonary disease manifestations, the plasma levels may reflect these differences. While the performance of cholestenone in sputum would fall short of the WHO target product profile for a TB disease biomarker in Peru, evaluating additional cholestenone-related species may lead to a superior test. A non-sputum based diagnostic is a high priority for TB diagnostics. In Peru, it was found that the ratio of cholestenone to cholesterol in plasma samples performed extremely well as a diagnostic for active TB (AUC=0.90). It will be critical to see if this can be improved upon and adapted to other populations.

It was also found that cholestenone levels in sputum correlated with the degree of smear positivity. If sputum cholestenone reflects disease burden, then sputum levels might be used to monitor treatment.

Homologs of 3β-Hsd have been annotated in the genomes of most NTM species, and we found that *M. abscessus* also produces cholestenone during infection. Thus, cholestenone might be a useful biomarker for NTM infections as well. While TB incidence has declined in the US, infections with NTM are rising. NTM infections require extremely long courses of treatment, usually more than a year, and they are often more challenging to treat than Mtb because of limited antibiotic options. Biomarkers that could guide clinical decision making would be extremely useful. While isolation of Mtb from a sputum sample is always diagnostic of TB infection, isolation of NTM can occur because of environmental contamination. Detection of cholestenone could be a rapid way to distinguish true infection from contamination. In addition, a mass spectrometry-based test is feasible in clinical microbiology laboratories in high income settings where NTM infections are an increasing problem.

Taken together the present example establishes cholestenone is a prominent metabolic signature of mycobacterial infections, and Mtb uses the cholesterol oxidase 3β-Hsd to produce it. While there are a number of Mtb-derived molecules that have been pursued for diagnostic and biomarker purposes, as far as we are aware, cholestenone is unique in being the result of active bacterial-host co-metabolism. Recent efforts to develop novel diagnostics and biomarkers have focused on detecting a distinctive signature of the host response to TB infection. One challenge for host-based diagnostics is that with clinical use, co-infections and co-morbidities impact the host signatures. Thus, to date there has been considerable progress identifying TB biomarkers, but efforts continue to be hampered by paucibacillary disease and heterogeneity of the host response.

Figure 8:
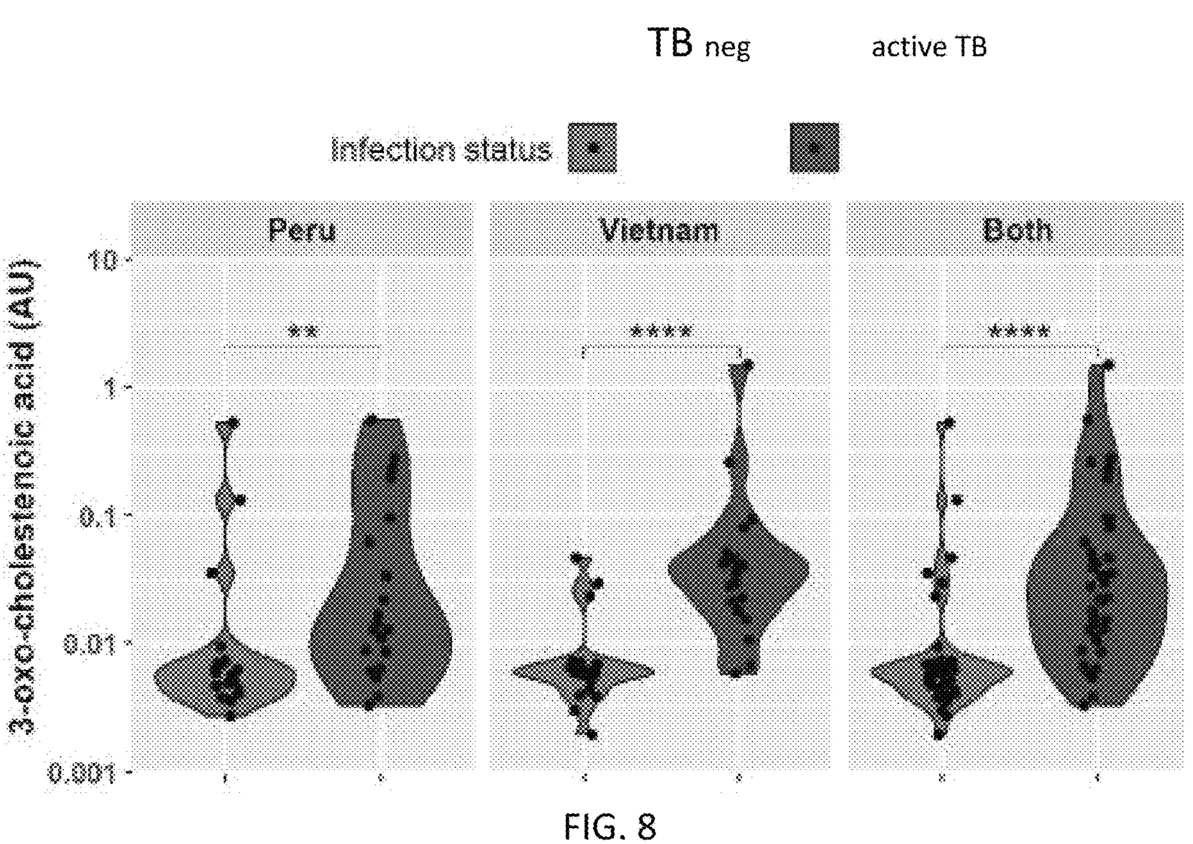
FIG. 8 shows 3-Oxocholestenoic acid levels are elevated in sputum samples from TB patients in Peru and Vietnam. Levels of 3-oxocholestenoic acid in sputum from TB negative (n=20 per country) and TB positive subjects (n=20 per country). Note: the y-axis is a log scale. AU—arbitrary units; p<0.01/**p<0.0001 (Mann-Whitey test).
Figures 9A, 9B:
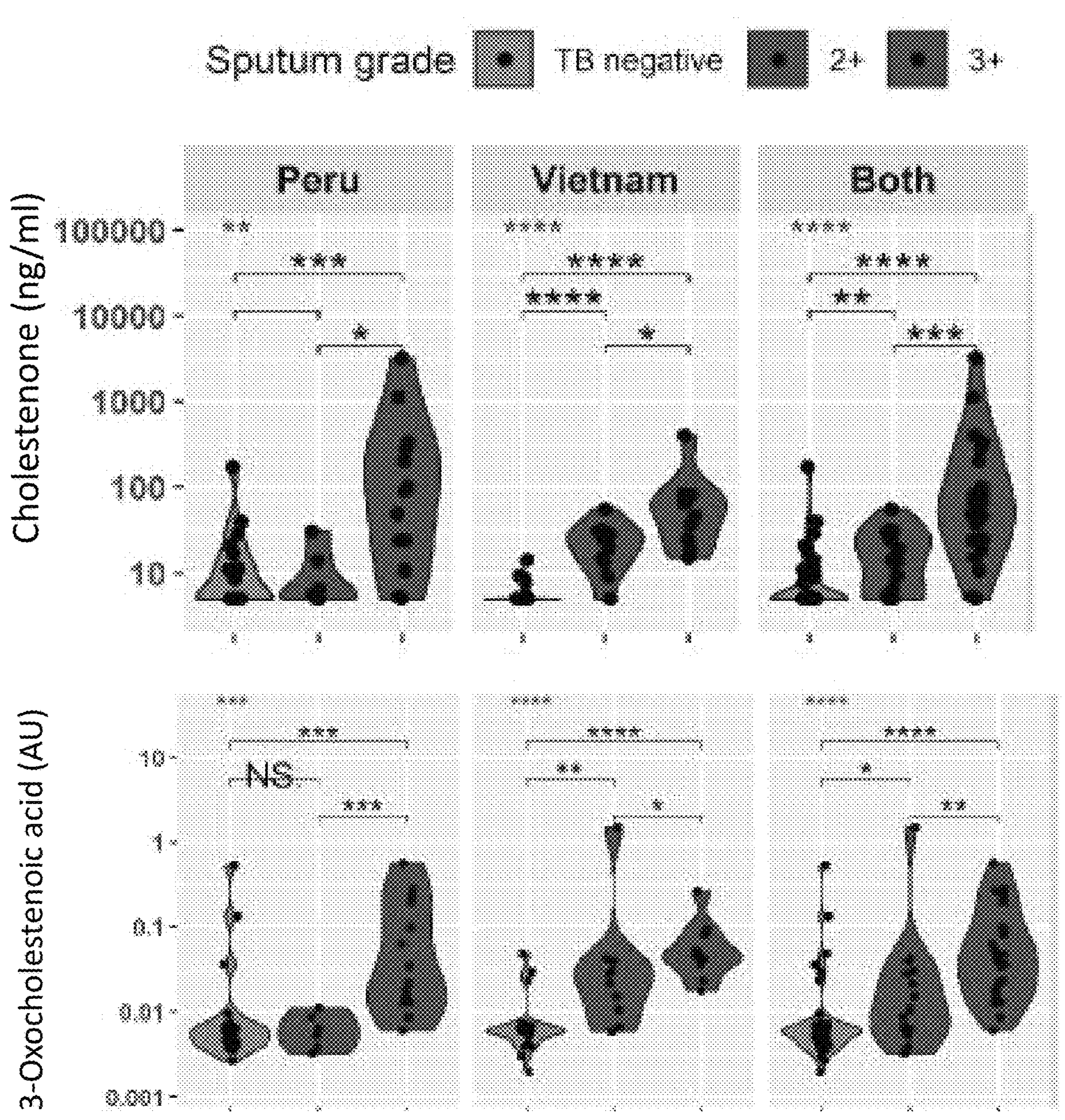
FIG. 9 shows cholestenone and 3-oxocholestenoic acid abundance in sputum of patients with active TB correlates with smear grade. Levels of cholestenone and 3-oxocholestenoic acid are plotted for TB negative subjects and TB positive subjects grouped according to sputum grade. Results are shown for each country (n=40) as well as both countries pooled (n=80). Statistical analyses used the Kruskal-Wallis test (blue asterisks) followed by pairwise comparisons with the Mann-Whitney test (black asterisks). *p<0.05, p<0.01, *p<0.001, ****p<0.0001. NS and lack of asterisks indicates p>0.05.
Figure 10:
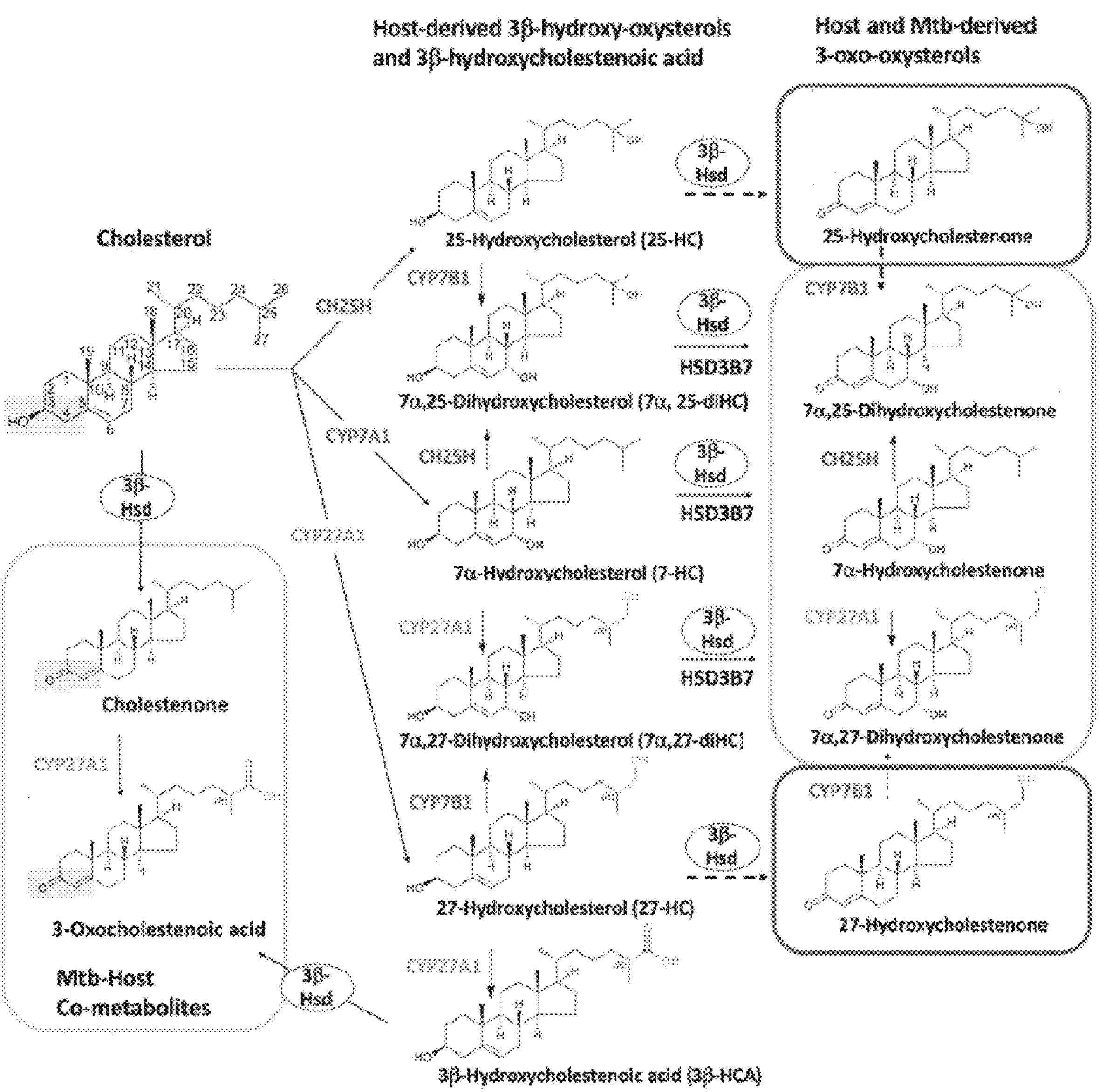
FIG. 10 shows the structure of cholesterol, 3β-hydroxy- and 3-oxo-oxysterols and cholestenoic acids. Structure of cholesterol is shown with carbon atoms numbered. CH25H, CYP7A1, CYP7B1, and CYP27A1 generate 3β-hydroxy-oxysterols. The color of the enzyme name matches the color of the hydroxy group that it adds. CYP27A1 further converts 27-HC to 3β-HCA (which has a carboxylic acid, in orange). Metabolites in the blue box are increased in the sputum of subjects with active TB. Cholestenone is made by Mtb 3β-Hsd converting cholesterol to cholestenone. 3-Oxocholestenoic acid could be made by host CYP27A1 using cholestenone as a substrate or Mtb 3β-Hsd using 3β-HCA as a substrate. The metabolites in the pink box can be generated by both Mtb 3β-Hsd and human HSD3B7. In the red boxes are candidate 3-oxo-oxysterols generated by Mtb 3β-Hsd that cannot also be generate by HSD3B7 because the 7α-hydroxy group is mandatory for HSD3B7 activity.

Example 2-3-Oxocholestenoic Acid is Elevated in Sputum Samples from TB Patients Lungs are a major source of 3β-hydroxycholestenoic acid (3β-HCA), reflecting the high level of CYP27A1 expression in alveolar macrophages. Therefore, it was investigated if Mtb 3β-Hsd was modifying oxysterols more broadly and not just cholesterol. Methods were developed to measure 3β-HCA and 3-oxocholestenoic acid from clinical samples. Indeed, much as what was observed for cholestenone, 3-oxocholestenoic acid was elevated in the sputum of subjects with active TB relative to TB-negative controls in both Peru and Vietnam (FIG. 8). In addition, there was a correlation between smear-grade and 3-oxocholestenoic acid levels, as had been seen for cholestenone (FIG. 9). 3-Oxocholestenoic acid could arise from macrophage CYP27A1 metabolizing cholestenone or Mtb 3β-Hsd metabolizing 3β-HCA (or both). In either case, the finding that both cholestenone and 3-oxocholestenoic acid are elevated in subjects with TB supports the assertion that Mtb shifts the oxysterol landscape from 3β-hydroxy to 3-oxo metabolites, of which are useful for detecting and monitoring infection.

24S—HC, 25-HC, 27-HC, 7α-HC, 7β-HC, 7α,25-diHC, 7α,27-diHC, 3β-HCA, 3β-hydroxycholenoic acid, and their 3-oxo derivatives are detected and quantified in human samples using mass spectrometry. sputum and plasma from the Peruvian and Vietnamese subjects from our studies described above are analyzed. The sputum samples are liquified with Sputolysin (Calbiochem), and both sputum and plasma extracted with 80% methanol for 10 minutes as described above. Samples are spiked during methanol extraction with pre-measured, isotope-labelled standards (33-hydroxysterols are available as OxysteroISPLASH from Avanti Polar Lipids Inc while 3-oxosterols are available from the Griffiths-Wang lab), which are used for metabolite identification and absolute quantification according to a detailed published protocol (48). Briefly, hydroxysterols, cholestenoic acids, and their 3-oxo analogues are separated from cholesterol and sterols of similar hydrophobicity by solid phase extraction. Enzyme-assisted derivatization for sterol analysis (EADSA) is used to enhance the signal in subsequent LC-electrospray ionization (ESI)-MS analysis. Samples are split into two fractions. Fraction A is treated with cholesterol oxidase from *Streptomyces* sp (Merck) which, like Mtb 3β-Hsd, converts 3β-hydroxy cholesterols to 3-oxo-versions, which will subsequently be derivatized with [2H5]Girard's P hydrazine. Fraction B are not be treated with *Streptomyces* cholesterol oxidase, so only the 3-oxo metabolites that are already present in the sample will be derivatized, this time by [2H0]Girard P hydrazine. Deconvolution of the data to determine the quantity of 3β-hydroxysterols (fraction A-fraction B), while fraction B provides the quantities of endogenous 3-oxosterols. Samples will be analyzed by LC-MS(MS3) on a high-resolution Orbitrap mass spectrometer (Orbitrap Elite or Orbitrap IDX). We will measure free metabolites, not esterified, since these are the biologically active compounds. From a 100 μl sample, we can successfully quantify all of the proposed oxysterols as well as many others. The assays are highly sensitive with a limit of quantitation (LOQ) of 0.1 ng/ml. For example, in 100 μl of the National Institute of Standards and Technology (NIST) SRM 1950 plasma, we can successfully quantify the 3-oxo version of 27-HC at 0.5 ng/ml. The TB infected samples will have higher 3-oxo sterols than the NIST reference plasma. The metabolites are stable under −80° storage conditions; the NIST SRM 1950 plasma sample was made in 2006 from pooled human plasma (from healthy individuals with a gender balance and ethnic distribution representative of the US population), and it is still used as a reference standard.

What is claimed is:

1. A method of treating a subject in need thereof with tuberculosis, a non-tuberculous mycobacteria infection, a Rhodococcus infection, or a Nocardia infection, the method comprising:

a) measuring levels of one or more of a cholesterol, an oxidated cholesterol derivative, an oxysterol, a 3β-hydroxycholestenoic acid, a 3-oxocholestenoic acid, and a 3-oxo-oxysterol, in a biological sample obtained from the subject;

b) administering a treatment comprising an effective amount of a corticosteroid or at least one antibiotic selected from the group consisting of rifampicin, isoniazid, pyrazinamide, and ethambutol to the subject, wherein the subject has been determined to have an increased level of one or more of the oxidated cholesterol derivative, the 3-oxocholestenoic acid, and the 3-oxo-oxysterol in the biological sample relative to a respective reference value obtained from a healthy control based upon the measurement in step a).

2. The method of claim 1, wherein the biological sample is selected from at least one of serum, plasma, and/or sputum.

3. The method of claim 1, wherein the oxidated cholesterol derivative is cholestenone and the method further comprising-comprises determining the ratio value of cholestenone to cholesterol wherein an increase in the cholestenone to cholesterol ratio indicates the subject has tuberculosis, a non-tuberculous *mycobacteria* infection, a *Rhodococcus* infection or a *Nocardia* infection.

4. The method of claim 3, wherein the level of cholestenone is determined from a sputum sample obtained from the subject and the level of cholesterol is determined from a plasma sample obtained from the subject or wherein the level of cholestenone and the level of cholesterol is determined from a plasma sample obtained from the subject.

5. The method of claim 1, further comprising determining the ratio value of the 3-oxocholestenoic acid to the 3β-hydroxycholestenoic acid and/or the ratio value of the 3-oxo-oxysterol to the 3β-hydroxy-oxysterol; and wherein an increase in the 3-oxocholestenoic acid to 3β-hydroxycholestenoic acid ratio value or an increase in the ratio value of 3-oxo-oxysterol to 3β-hydroxy-oxysterol indicates the subject has tuberculosis, a non-tuberculous *mycobacteria* infection, a *Rhodococcus* infection, or a *Nocardia* infection.

6. The method of claim 5, wherein the oxysterol is one or more of 25-hydroxycholesterol, 7α25-hydroxycholesterol, 7α-hydroxycholesterol, 7α27-hydroxycholesterol, and 27-hydroxycholesterol; and/or the 3-oxo-oxysterol is one or more of 25-hydroxycholestenone, 7α-25-hydroxycholestenone, 7α-hydroxycholestenone, 7α27-hydroxycholestenone, and 27-hydroxycholestenone.

7. The method of claim 6, wherein the ratio value of the 3-oxo-oxysterol to the 3β-hydroxy-oxysterol is the ratio value of one or more of 25-hydroxycholesternone to 25-hydroxycholesterol ratio, 7α25-hydroxycholestenone to α25-hydroxycholesterol ratio, 7α-hydroxycholestenone to 7α-hydroxycholesterol ratio, 7α27-hydroxycholestenone to 7α27-hydroxycholesterol ratio, and 27-hydroxycholestenone to 27-hydroxycholesterol ratio.

8. The method of claim 1, wherein the levels of one or more of cholesterol, an oxidated cholesterol derivative, an oxysterol, a 3β-hydroxycholestenoic acid, 3-oxocholestenoic acid, and a 3-oxo-oxysterol are determined using liquid chromatography-high resolution mass spectrometry.

9. The method of claim 1, wherein the subject is at risk of developing tuberculosis or the non-tuberculous *mycobacteria* infection, *Rhodococcus* infection, or *Nocardia* infection, has signs and/or symptoms of tuberculosis or the non-tuberculous *mycobacteria* infection, *Rhodococcus* infection or *Nocardia* infection, or is diagnosed with tuberculosis or the non-tuberculous *mycobacteria* infection, *Rhodococcus* infection or *Nocardia* infection.

10. The method of claim 1, wherein the method further comprises detecting the levels of one or more of itaconate, methylsuccinate, methylcitrate, 2-aminoadipate, and propionylcarnitine.

11. A method of treating a subject in need thereof having a tuberculosis, a non-tuberculous mycobacteria infection, a Rhodococcus infection, or a Nocardia infection, the method comprising:

a) quantifying, in a first biological sample obtained from the subject, levels of one or more of a cholesterol, an oxidated cholesterol derivative, an oxysterol, 3β-hydroxycholestenoic acid, a 3-oxocholestenoic acid, and a 3-oxo-oxysterol;

b) administering a first dose of a corticosteroid or at least one antibiotic selected from the group consisting of rifampicin, isoniazid, pyrazinamide, and ethambutol to the subject, wherein the subject has been determined to have an increased level of one or more of oxidated cholesterol derivative, 3-oxocholestenoic acid, and the 3-oxo-oxysterol in the biological sample relative to respective reference value obtained from a healthy control based upon the measurement in step a);

c) quantifying, in a second biological sample obtained from the subject after the treatment, one or more of the cholesterol, oxidated cholesterol derivative, oxysterol, 3β-hydroxycholestenoic acid, 3-oxocholestenoic acid, and 3-oxo-oxysterol and i) detecting no change or a decrease in the amount of the one or more of cholesterol, oxidated cholesterol derivative, 3-oxocholestenoic acid, or 3-oxo-oxysterol in the second sample, as compared to the first sample; or (ii) detecting an increase in one or more of cholesterol, oxidated cholesterol derivative, 3-oxocholestenoic acid, or 3-oxo-oxysterol increases in the second sample as compared to the first sample wherein the increase is less than an increase that occurs in a control group of subjects with the same infection but were not administered treatment; and d) administering a second dose of the corticosteroid or the at least one antibiotic to the subject, wherein the second dose administered is adjusted based up on the no change, decrease, or increase in the amount of the one or more of the cholesterol, oxidated cholesterol derivative, 3-oxocholestenoic acid, or 3-oxo-oxysterol in the second sample relative to respective reference value obtained from a healthy control.

12. The method of claim 11, wherein the first and second biological sample are the same and are at least one of-serum, plasma and/or sputum.

13. The method of claim 11, wherein the level of cholesterol in the second biological sample increases or remains the same relative as the level of cholesterol in the first biological sample.

14. The method of claim 11, wherein the oxidated cholesterol derivative is cholestenone and wherein the method further comprises determining the ratio value of cholesterone to cholesterol in the first and second biological sample and wherein step (c)(i) comprises detecting a decrease or no change in the cholesterone to cholesterol ratio in the second biological sample compared to the first biological sample.

15. The method of claim 14, wherein the level of cholestenone is determined from a sputum sample obtained from the subject and the level of cholesterol is determined from a plasma sample obtained from the subject or wherein the level of cholestenone and the level of cholesterol is determined from a plasma sample obtained from the subject.

16. The method of claim 11, wherein the oxysterol is one or more of 25-hydroxycholesterol, 7α25-hydroxycholesterol, 7α-hydroxycholesterol, 7α27-hydroxycholesterol, and 27-hydroxycholesterol; and/or wherein the 3-oxo-oxysterol is one or more of 25-hydroxycholestenone, 7α25-hydroxycholestenone, 7α-hydroxycholestenone, 7α27-hydroxycholestenone, and 27-hydroxycholestenone.

17. The method of claim 11, further comprising determining the ratio value of the 3-oxocholestenoic acid to the 3β-hydroxycholestenoic acid in the first and second biological samples and detecting a decrease or no change in the 3-oxocholestenoic acid to 3β-hydroxycholestenoic acid ratio value in the second biological sample compared to the first biological sample; or determining the ratio value of 3-oxooxysterol to 3β-hydroxy-oxysterol in the first and second biological samples and detecting a decrease or no change in the ratio value of 3-oxo-oxysterol to 3β-hydroxy-oxysterol in the second biological sample compared to the first biological sample.

18. The method of claim 17, wherein the ratio value of the 3-oxo-oxysterol to the 3β-hyroxy-oxysterol is the ratio value of one or more of 25-hydroxycholestenone to 25-hydroxycholesterol ratio, 7α25-hydroxycholestenone to α25-hydroxycholesterol ratio, 7α-hydroxycholestenone to 7α-hydroxycholesterol ratio, 7α27-hydroxycholestenone to 7α27-hydroxycholesterol ratio, and 27-hydroxycholestenone to 27-hydroxycholesterol ratio.

19. The method of claim 11, wherein the levels of one or more of cholesterol, the oxidated cholesterol derivative, the oxysterol, the 3β-hydroxycholestenoic acid, the 3-oxocholestenoic acid, and a 3-oxo-oxysterol are determined using liquid chromatography-high resolution mass spectrometry.

20. The method of claim 11, wherein the method further comprises detecting the levels of one or more of itaconate methylsuccinate, methylcitrate, 2-aminoadipate, and propionylcarnitine.

* * * * *